United States Patent
Scheideler et al.

(10) Patent No.: US 11,800,859 B2
(45) Date of Patent: Oct. 31, 2023

(54) RAT MODELS FOR CMT2A THAT DEVELOP A PROGRESSIVE NEUROPATHY

(71) Applicants: Charcot-Marie-Tooth Association, Chester, PA (US); The Trustees of the University of Pennsylvania, Philadelphia, PA (US)

(72) Inventors: Mark Albert Scheideler, Silver Spring, MD (US); Guojun Zhao, Saint Louis, MO (US); John Svaren, Madison, WI (US); David C. Chan, Pasadena, CA (US); Steven S. Scherer, Media, PA (US); Taleen Hanania, Valhalla, NY (US)

(73) Assignees: Charcot-Marie-Tooth Association, Glenolden, PA (US); Trustees of the University of Pennsylvania, Philadelphia, PA (US)

( * ) Notice: Subject to any disclaimer, the term of this patent is extended or adjusted under 35 U.S.C. 154(b) by 234 days.

(21) Appl. No.: 16/346,003

(22) PCT Filed: Oct. 30, 2017

(86) PCT No.: PCT/US2017/058952
§ 371 (c)(1),
(2) Date: Apr. 29, 2019

(87) PCT Pub. No.: WO2018/081675
PCT Pub. Date: May 3, 2018

(65) Prior Publication Data
US 2020/0053991 A1 Feb. 20, 2020

Related U.S. Application Data

(60) Provisional application No. 62/414,863, filed on Oct. 31, 2016.

(51) Int. Cl.
| | | |
|---|---|---|
| G01N 33/00 | (2006.01) |
| A01K 67/00 | (2006.01) |
| A01K 67/027 | (2006.01) |
| C12N 9/14 | (2006.01) |

(52) U.S. Cl.
CPC ............ *A01K 67/0278* (2013.01); *C12N 9/14* (2013.01); *A01K 2217/075* (2013.01); *A01K 2227/105* (2013.01); *A01K 2267/0356* (2013.01); *C12Y 306/05* (2013.01)

(58) Field of Classification Search
CPC .......... A01K 67/0275; A01K 2217/075; A01K 2227/105; A01K 2267/0356; C12N 9/14; G01N 33/00
See application file for complete search history.

(56) References Cited

PUBLICATIONS

Cartoni et al., 2010, Journal of Neurology, vol. 133, p. 1460-1469.*
Feely et al., 2011, Neurology, 76: 1690-1696.*
Patil et al., 2011, Indian Journal of Public Health research & Development, vol. 2, No. 1, p. 106-109.*
Khodarovich et al., 2013, Applied Biochemistry and Microbiology, vol. 49, No. 9, pp. 711-722.*
Selsby et al., 2015, ILAR Journal, vol. 56, No. 1, p. 116-126.*
Maksimenko et al., 2013, Acta Naturae, vol. 5, No. 1, p. 33-46.*
Yang et al., 2016, PNAS, 113(41), E6209-E6218, p. 1-10.*
Guo et al., 2015, Cell Research, vol. 25, p. 767-768.*
Lee et al., 2016, Drug Discovery Today: Disease Models, vol. 20, p. 13-20.*
Kang et al., 2018, Human Molecular Genetics, vol. 27, No. 2, p. 211-223.*
Kim et al., Jan. 21, 2016, US 20160015010 A1.*

* cited by examiner

*Primary Examiner* — Shin Lin Chen
(74) *Attorney, Agent, or Firm* — Joseph F. Aceto, Esq.

(57) ABSTRACT

The present invention relates to Charcot-Marie-Tooth disease 2A (CMT2A) harboring the p.Arg364Trp or p.His361Tyr Mfn2 mutation, whose human counterpart results in severe, early-onset axonal neuropathy for p.Arg364Trp Mfn2 mutation in fertilized rat eggs. Cohorts of mutants and wild type littermates were characterized with multiple motor deficits that worsened over time. Separate cohorts of mutant and wild type at 7, 40, and 48 weeks showed reduced density of myelinated axons and active axonal degeneration in distal but not proximal nerves, as well as axonal degeneration in the fasciculus gracilis of the cervical spinal cord at 40 and 48 weeks not present in 7-week-old cohort Mfn2 mutants, or wild type at 7 or 40 weeks. The p.His361Tyr Mfn2 mutation using CRISPR/Cas9 showed abnormalities in gait dynamics at 8 weeks and lengthening of gait cycle at 16 weeks. The invention provides progressive axonal neuropathy for examining pathogenesis and treatment of CMT2A.

5 Claims, 11 Drawing Sheets

Specification includes a Sequence Listing.

RAT MODELS FOR CMT2A THAT DEVELOP A PROGRESSIVE NEUROPATHY

CROSS REFERENCE

This application is the US national application of PCT/US2017/058952, filed on 30 Oct. 2017 which claims priority to U.S. Provisional Patent Application No. 62/414,863, filed Oct. 31, 2016, the disclosure of which is herein incorporated by reference in its entirety.

FIELD OF THE INVENTION

The present invention relates generally to the field of genetically heterogeneous peripheral neuropathies associated with Charcot-Marie-Tooth (CMT) disease. More specifically, the development of a genetic animal model for CMT2A demonstrating progressive axonal neuropathy for assessing the pathogenesis and treatment of CMT2A.

BACKGROUND OF THE INVENTION

Charcot-Marie-Tooth (CMT) neuropathy is a heterogeneous group of inherited diseases found in peripheral nerves. CMT is a common disorder affecting both children and adults. Charcot-Marie Tooth disease (CMT) or hereditary motor and sensory neuropathy (HMSN) are the most commonly used names for inherited neuropathies that are not part of a syndrome (Klein, C. J., Duan, X., Shy, M. E., 2013. Inherited neuropathies: Clinical overview and update. Muscle Nerve; Bassam, B., 2014. Charcot-Marie-Tooth Disease Variants—Classification, Clinical, and Genetic Features and Rational Diagnostic Evaluation. J. Clin. Neuromusc. Dis. 15, 117-128; Scherer, S. S., Shy, M. E., 2015. CMT Subtypes and Disease Burden in Patients Enrolled in the INC Natural History Study (6601) from 2009-2013. J. Neurol. Neurosurg. Psychiat. 86, 873-878). CMT is common, with an estimated prevalence of 1 in 2500 representing a number of genetically distinct disorders. More than 80 different genetic causes have been discovered, and these are classified according to whether demyelination, or, axonal loss appears to be the primary event in the pathogenesis. The dominantly inherited demyelinating forms (type 1 CMT disorders) are characterized by slow nerve conduction velocities (below 38 m/s in the motor nerves of the arms) as well as demyelinated and especially remyelinated axons in biopsied nerves; the dominantly inherited axonal forms (type 2 CMT disorders) have normal or slightly reduced velocities with reduced motor and sensory compound action potential amplitudes, and axonal loss is the chief finding in biopsied nerves.

Dominant mutations in Mitofusin2 (MFN2) gene cause CMT2A (Züchner, S., Mersiyanova, I. V., Muglia, M., Bissar-Tadmouri, N., Rochelle, J., Dadali, E. L., Zappia, M., Nelis, E., Patitucci, A., Senderek, J., Parman, Y., Evgrafov, O., de Jonghe, P., Takahashi, Y., Tsuji, S., Pericak-Vance, M. A., Quattrone, A., Battologlu, E., Polyakov, A. V., Timmerman, V., Schroder, J. M., Vance, J. M., 2004. Mutations in the mitochondrial GTPase mitofusin 2 cause Charcot-Marie-Tooth neuropathy type 2A. Nat Genet 36, 449-451). CMT2A is estimated to cause up to 7% of all CMT, and is the most common form of type 2 CMT (Fridman, V., Bundy, B., Reilly, M. M., Pareyson, D., Bacon, C., Burns, J., Day, J. W., Feely, S., Finkel, R. S., Grider, T., Kirk, C., Herrmann, D. N., Laura, M., Li, J., Lloyd, T., Sumner, C., Muntoni, F., Ramchandren, S., Shy, R., Siskind, C. E., Yum, S. W., Moroni, I., Pagliano, E., Züchner, S., Scherer, S. S., Shy, M. E., 2015. CMT Subtypes and Disease Burden in Patients Enrolled in the INC Natural History Study (6601) from 2009-2013. J. Neurol. Neurosurg. Psychiat. 86, 873-878). Different MFN2 mutations cause different degrees of neuropathy. Most MFN2 mutations cause a severe, early onset, axonal neuropathy, and most are de novo mutations, and other dominant MFN2 mutations cause a milder axonal neuropathy with a later onset (Lawson, V. H., Graham, B. V., Flanigan, K. M., 2005. Clinical and electrophysiologic features of CMT2A with mutations in the mitofusin 2 gene. Neurology 65, 197-204; Chung, K. W., Kim, S. B., Park, K. D., Choi, K. G., Lee, J. H., Eun, H. W., Suh, J. S., Hwang, J. H., Kim, W. K., Seo, B. C., Kim, S. H., Son, I. H., Kim, S. M., Sunwoo, I. N., Choi, B. O., 2006. Early onset severe and late-onset mild Charcot-Marie-Tooth disease with mitofusin 2 (MFN2) mutations. Brain 129, 2103-2118; Verhoeven, K., Claeys, K. G., Züchner, S., Schroder, J. M., Weis, J., Ceuterick, C., Jordanova, A., Nelis, E., De Vriendt, E., Van Hul, M., Seeman, P., Mazanec, R., Saifi, G. M., Szigeti, K., Mancias, P., Butler, I. J., Kochanski, A., Ryniewicz, B., De Bleecker, J., Van den Bergh, P., Verellen, C., Van Coster, R., Goemans, N., Auer-Grumbach, M., Robberecht, W., Rasic, V. M., Nevo, Y., Tournev, I., Guergueltcheva, V., Roelens, F., Vieregge, P., Vinci, P., Moreno, M. T., Christen, H. J., Shy, M. E., Lupski, J. R., Vance, J. M., De Jonghe, P., Timmerman, V., 2006. MFN2 mutation distribution and genotype/phenotype correlation in Charcot-Marie-Tooth type 2. Brain 129, 2093-2102; Feely, S. M. E., Laura, M., Siskind, C. E., Sottile, S., Davis, M., Gibbons, V. S., Reilly, M. M., Shy, M. E., 2011, MFN2 mutations cause severe phenotypes in most patients with CMT2A. Neurology 76, 1690-1696). Recessive MFN2 mutations also cause severe, early onset, axonal neuropathy. Some dominant mutations in MFN2 produce myelopathy or optic atrophy; these complicated forms of CMT2 are sometimes referred to HMSN-V and HMSN-VI, respectively, but are not only caused by MFN2 mutations (Scherer, S. S., Kleopa, K. A., Benson, M. D., 2015. Peripheral neuropathies., in: Rosenberg, R. N., Pascual, J. M. (Eds.), Rosenberg's Molecular and Genetic Basis of Neurological and Psychiatric Disease, 5th ed. Elsevier, Philadelphia, pp. 1051-1074).

MFN2 is a nuclear gene that encodes an intrinsic membrane protein of the mitochondrial outer membrane. An ortholog has been identified in all eukaryotes, including yeast. Mammals have two mitofusin genes, Mfn1 and Mfn2, which have distinct but overlapping distributions, and both of which can promote mitochondrial fusion through trans-interactions (Chen, H., Chan, D. C., 2005. Emerging functions of mammalian mitochondrial fusion and fission. Hum. Mol. Genet. 14, R283-R289). Nearly all of the mutations in the MFN2 gene cause amino acid substitutions as single point mutations, including but not restricted to the GTPase domain (Cartoni, R., Martinou, J. C., 2009. Role of mitofusin 2 mutations in the physiopathology of Charcot-Marie-Tooth disease type 2A. Exp. Neurol. 218, 268-273). Because loss-of-function mutations of MFN2 also cause a severe axonal neuropathy (Nicholson, G. A., Magdelaine, C., Zhu, D., Grew, S., Ryan, M. M., Sturtz, F., Vallat, J. M., Ouvrier, R. A., 2008. Severe early-onset axonal neuropathy with homozygous and compound heterozygous MFN2 mutations. Neurology 70, 1678-1681), and result in reduced mitochondrial fusion (Chen, H., Chan, D. C., 2005. Emerging functions of mammalian mitochondrial fusion and fission. Hum. Mol. Genet. 14, R283-R289), it is possible that dominant MFN2 mutations have a dominant-negative effect on mitochondrial fusion (Detmer, S. A., Chan, D. C., 2007. Complementation between mouse Mfn1 and Mfn2 protects mitochondrial fusion defects caused by CMT2A disease mutations. J. Cell Biol. 176, 405-414: Baloh, R. H., Schmidt, R. E., Pestronk, A., Milbrandt, J., 2007. Altered axonal mitochondrial transport in the pathogenesis of Charcot-Marie-Tooth disease from mitofusin 2 mutations. J Neurosci 27, 422-430; Misko, A., Jiang, S., Wegorzewska, I., Milbrandt, J., Baloh, R. H., 2010. Mitofusin 2 is necessary for transport of axonal mitochondria and interacts with the Miro/Milton complex. J Neurosci 30, 4232-4240: Misko, A. L., Sasaki, Y., Tuck, E., Milbrandt, J., Baloh, R. H., 2012. Mitofusin2 mutations disrupt axonal mitochondrial positioning and promote axon degeneration. J Neurosci 32, 4145-4155).

The lack of an animal model has hindered investigation of how dominant MFN2 mutations cause peripheral neuropathy. An animal model for CMT2A demonstrating a progressive neuropathy would be a valuable tool for examining the pathogenesis, diagnosis, and treatment of CMT2A. Here we disclose knock-in rat models of the p.Arg364Trp (R364W) and p.His361Tyr (H361Y) mutations. A behavioral phenotype is evident in rats expressing the R364W mutation at 7 weeks, and evolves over 52 weeks. Histological analysis demonstrates that myelinated axons are normal at 7 weeks age, but there is pronounced axonal loss by 40 weeks of age, mainly of the longest myelinated axons in the peripheral nerves and cervical spinal cord. H361Y mutants show abnormalities in gait dynamics at 8 weeks and a lengthening of the gait cycle at 16 weeks.

BRIEF SUMMARY OF THE INVENTION

The present invention provides a genetically authentic CMT2A animal model harboring either the R364W or H361Y mutation, both of which cause a severe, early-onset axonal neuropathy, as well as myelopathy and optic atrophy phenotype in humans. R364W mutant rats develop a length-dependent axonal neuropathy in the peripheral nerves and in the fasciculus gracilis, both of which appear after 7 weeks of age.

One embodiment of the present invention is a R364W mutant rat model which is the first dominant Mfn2 mutation that develops a robust neuropathy. The progressive axonal neuropathy over time in this rat model reflects CMT2A progression in humans. Prior attempts to generate a CMT2A mouse model have failed to produce a progressive axonal neuropathy.

Surprisingly, the R364W rat model in the present invention produced a much more robust axonopathy than did the prior mouse models. One possible explanation is that the R364W mutation itself has a more severe effect. It is also possible that longer axons in rats compared to mice unmask the deleterious effects of the R364W mutation.

Further embodiments of the present invention include models using the R364W mutation that provide for actively degenerating myelinated axons. The R364W mutation elicits fewer myelinated axons in the distal aspect of the tibial and sural nerves compared to control, but not in the distal femoral nerve which is much shorter in 40-week-old mutant rats. These findings were not present in 7-week-old rats, demonstrating that the length- and time-dependence of axonal loss in this animal model, features that are thought to be characteristic of most axonal neuropathies, including CMT2A.

Actively degenerating myelinated axons are restricted to the fasciculus gracilis in the cervical spinal cord in 40-week-old R364W mutant rats. These findings confirm prior reports of axonal degeneration in the fasciculus gracilis with homozygous Mfn2 mutations. The cervical fasciculus gracilis is comprised of myelinating axons that originate from mechanoreceptors in the lumbar region, and hence are the longest sensory axons in the cervical spinal cord. The axonal loss in the dorsal columns has been attributed to the loss of sensory neurons in the dorsal root ganglia. The loss of these centrally directed axons would contribute to diminished sensation, so preventing this loss would be a goal of therapeutic interventions.

The inventors of the present invention discovered that many of the large axons in 40-week-old mutant femoral motor nerves from mutant rats were thinly myelinated; these likely belong to alpha-motoneurons. Because these axons were normally myelinated in 7-week-old mutant femoral motor nerves, it is suspected that these axons had been demyelinated then remyelinated between 7 and 40 weeks. Because axonal diseases seldom cause demyelination, this finding suggests that the R364W mutation has direct effects on myelinating Schwann cells.

Like other mutations associated with severe, early-onset axonal neuropathy, the chief finding is severe axonal loss; one biopsy also showed clusters of regenerated axons.

Given the severity of neuropathy at 40 weeks, it is anticipated that the longitudinal analysis of behavioral profiling would reveal a progressive deterioration of sensory and motor function in R364W mutant rats.

In another aspect, performance of the rat model in the horizontal ladder test to assess subtle motor coordination effects through foot slips showed significant deficits in hind limb performance at 30 weeks of age, which greatly worsened at advanced age (one year). The sensitive multi-parametric gait analysis demonstrated severely affected gait performance that was further revealed to represent paw positioning and presentation, and an unstable, hesitant and splayed pattern of leg movement. The changes were progressive, with strong significance achieved with multiple gait measures at one year of age, and early progressive change (7-19 weeks of age) observed for fine measures of paw positioning and imaging.

In addition, H361Y mutant rats show abnormalities in gait dynamics in both forelimbs and hind limbs at 8 weeks with a lengthening of the gait cycle by 16 weeks. Further, there is a reduction in the density of myelinated axons and actively degenerating myelinated axons by 32 weeks.

The H361Y mutant rat model elicits abnormalities in gait dynamics. These animals demonstrate a shorter stand duration in both forelimbs and hind limbs compared to normal rats. In addition, the H361Y mutant rats have an increased base width, of the forelimbs at 8 weeks although changes in hind limb base width were not detected at the 8 week time point. At 16 weeks, the animals showed a shorter stand duration in both forelimbs and hind limbs. Further at 16 weeks, the H361Y mutant rats have an increased step length and swing duration, indicating a lengthening of the gait cycle. These characteristics provide a model for assessing faster gait cycles with an indication of earlier deficits in forelimbs in subjects expressing the CMT2A mutation. In addition, the H361Y mutant rats expressed features in body motion and paw position that were different from the same features observed in normal rats.

H361Y mutants show a reduced density of myelinated axons and actively degenerating myelinated axons in 32 week old rats in the distal tibial nerve.

Both mutations exemplify models that are valuable tools for examining the pathogenesis and treatment of CMT2A. The invention relates to genetically modified rats, as well as the descendants and ancestors of such animals, which are animal models for human CMTA2 and methods for their use.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

Upper diagram indicates the functional domains of the Mitofusin 2 protein along with the position of the p.Arg364Trp mutation, which was inserted into the rat genome as described in the Description. PCR fragments from genomic DNA of the transgenic male were sequenced to verify the mutation in rats heterozygous (HET) for the mutation, which is shown in the lower panel.

Figure 2:
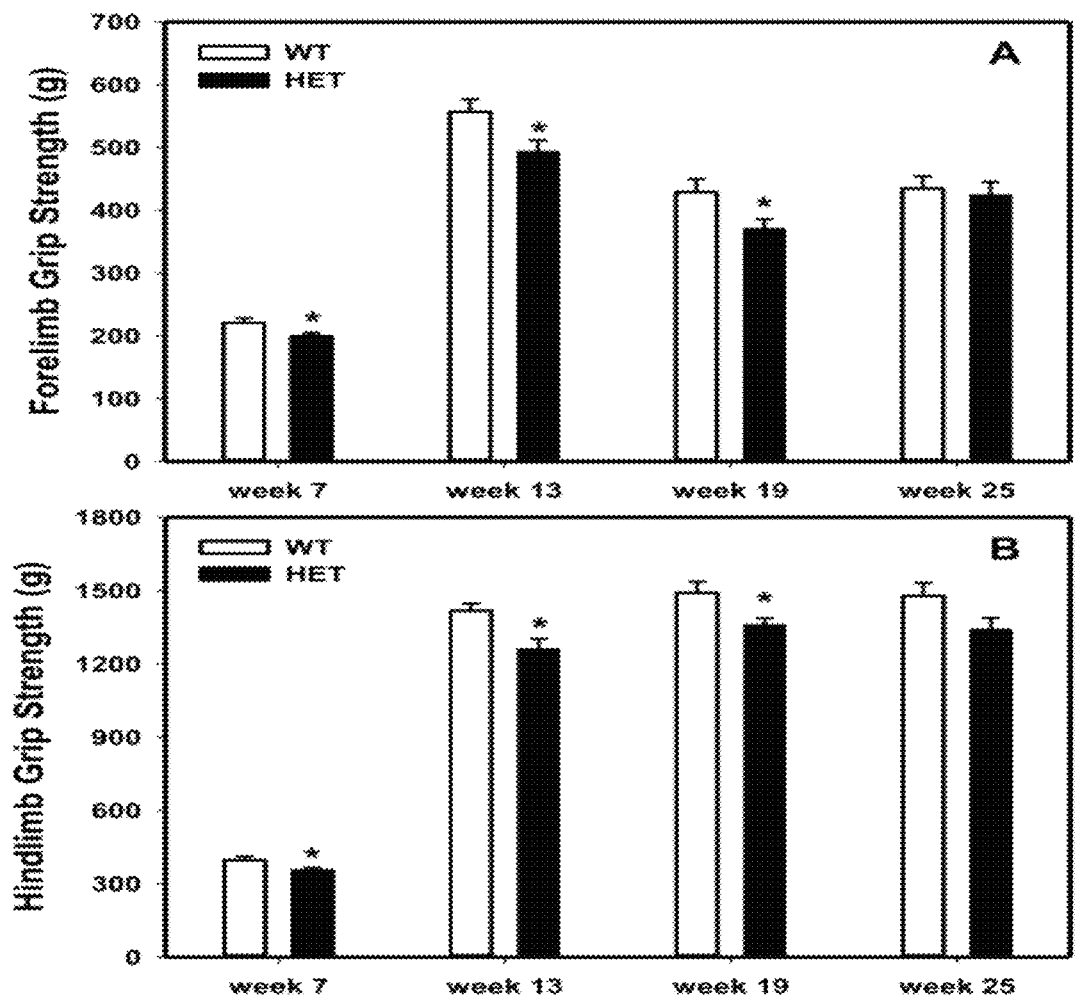

FIG. 2: R364W mutant rats have reduced grip strength.

Cohorts of male rats heterozygous for the R364W Mfn2 mutation (HET, n=20) and their wild type male littermates (WT; n=20) were tested at the ages indicated. At week 7, two statistical outliers were removed from the analysis of the hind limb grip strength. The means and standard deviations are shown; asterisks denote significant differences between the HET and WT rats (Student's unpaired t-test; $p<0.05$). Heterozygous R364W Mfn2 HET male rats have reduced forelimb and hindlimb strength compared to their WT male littermates at 7, 13, and 19 weeks, representing changes of 10, 11, and 13 percent (forelimb), and changes of 11, 10 and 9 percent (hindlimb), respectively. No significant difference was observed at 25 weeks.

Figure 3:
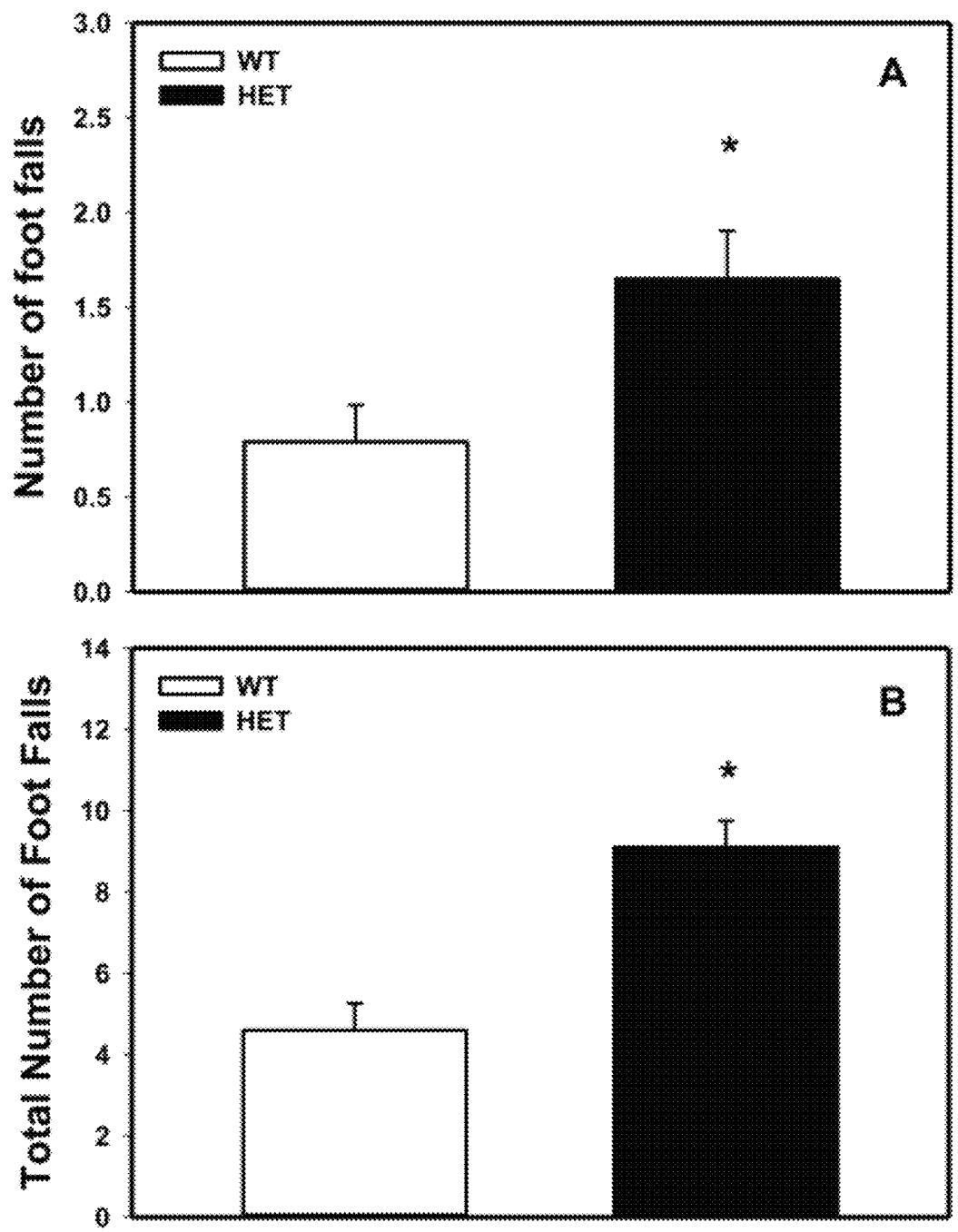

FIG. 3: R364W mutant rats have more hind limb foot slips at 30 and 52 weeks of age. Cohorts of male rats heterozygous for the R364W mutation rats (HET) and their wildtype (WT) male littermates were tested on a horizontal ladder at 30 and 52 weeks, Panel A and B respectively. Group sizes for week 30 were n=20, whereas the p.R364W HET male group was n=18 at month 12. The means and standard deviations are shown; asterisks denote significant differences between the HET and WT rats (Student's unpaired t-test; $p<0.05$). HET male rats had more hind limb foot slips at 30 and 52 weeks of age than did their WT male littermates (Student's unpaired t-test; $p<0.05$). Values for HET rats at 30 and 52 weeks of age were 1.7+/−0.3 (SEM) and 9.2+/−0.6 (SEM), respectively. This compared to values for WT rats at 30 and 52 weeks of age of 0.8+/−0.2 (SEM) and 4.6+/−0.7 (SEM), respectively.

Figure 4:
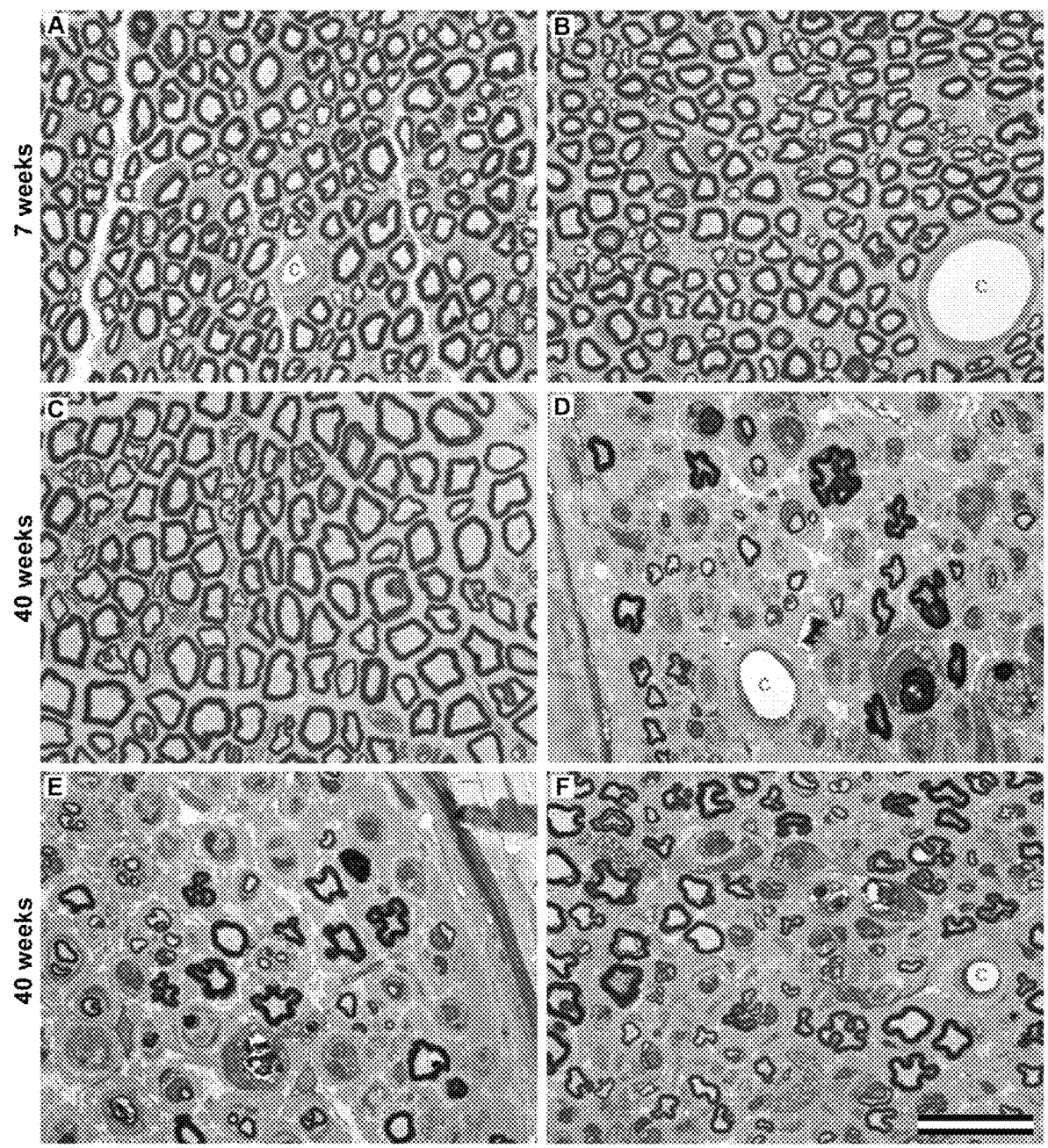

FIG. 4: Pathological findings in distal tibial nerves of R364W mutant rats. These are images of semi-thin sections of the distal tibial nerve (at the ankle) from 7-week-old (A, B) and 40-week-old (C—F) rats. Panels (A) and (B), from a 7-week-old male wildtype rat and male rat heterozygous for the R364W mutation, respectively, show no apparent pathology. Compared to a 40-week-old wildtype male rat (C), 3 different 40-week-old R364W mutant rats showed several pathological features (D-F): the density of myelinated axons is reduced; actively degenerating myelinated axons (arrows), lipid-filled cells (either Schwann cells or macrophages; arrowheads), and clusters of regenerating axons (dotted circles) are found throughout the endoneurium. C: capillary. Scale bar: 100 microns.

Figure 5:
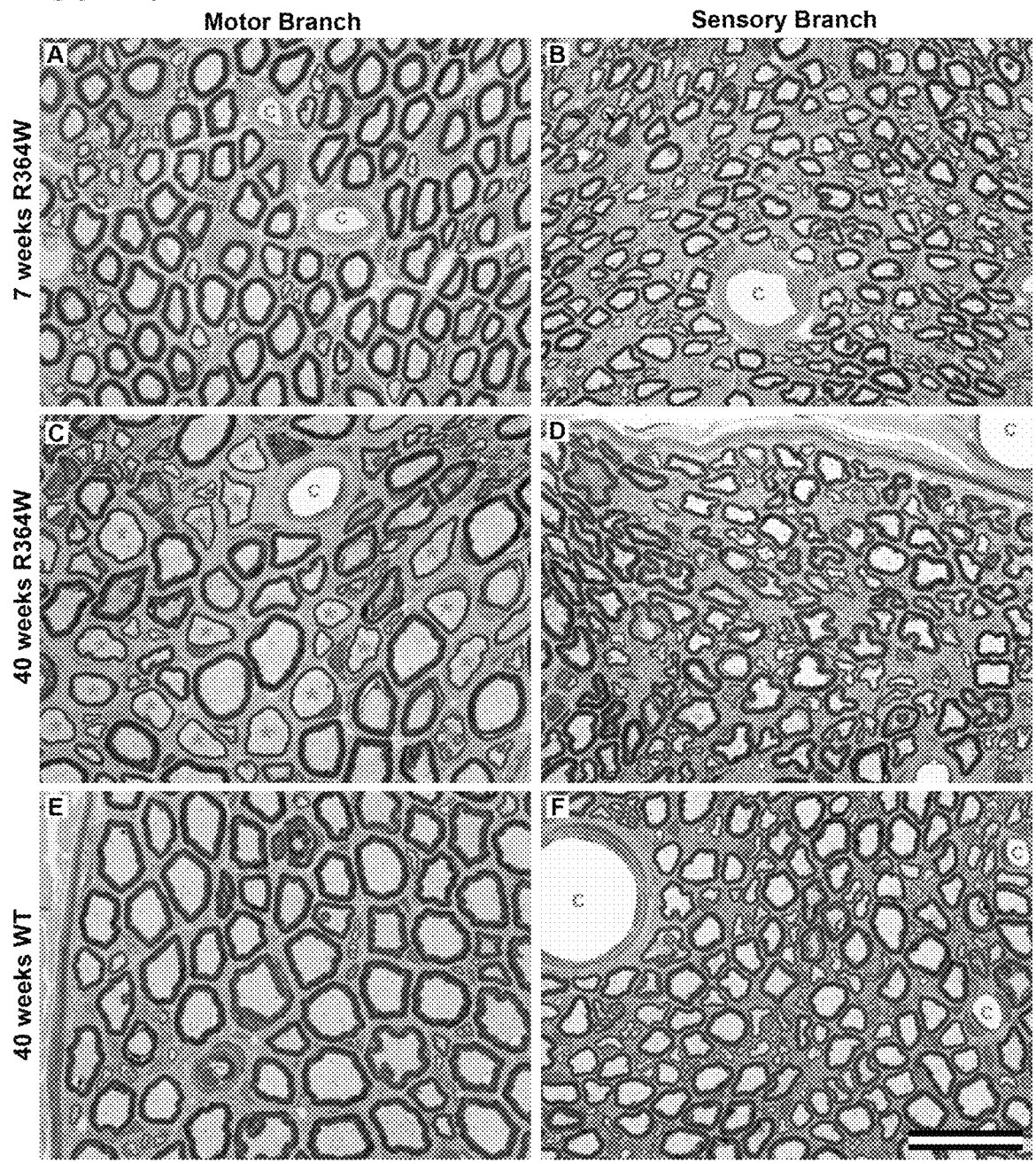

FIG. 5: Pathological findings in femoral motor nerves of R364W mutant rats. These are images of semi-thin sections of the motor and sensory branches of the distal femoral nerve from 7-week-old (A, B) and 40-week-old (C—F) rats. The femoral motor branch from a 40-week-old male rat heterozygous for the R364W mutation (C) contains many myelinated axons that have disproportionately thin myelin sheaths for their axonal caliber (starred); these are not seen in the femoral motor branch of either a 7-week-old R364W mutant rat (A) or a 40-week-old wildtype male rat (E). The sensory branch looks normal in all examples. C: capillary. Scale bar: 100 microns.

Figure 6:
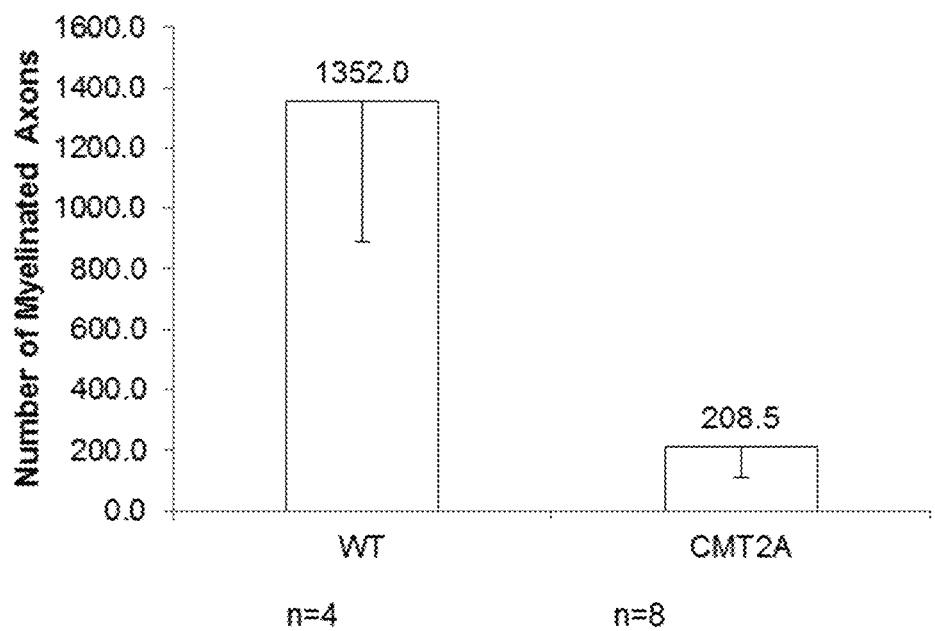
Figure 6:
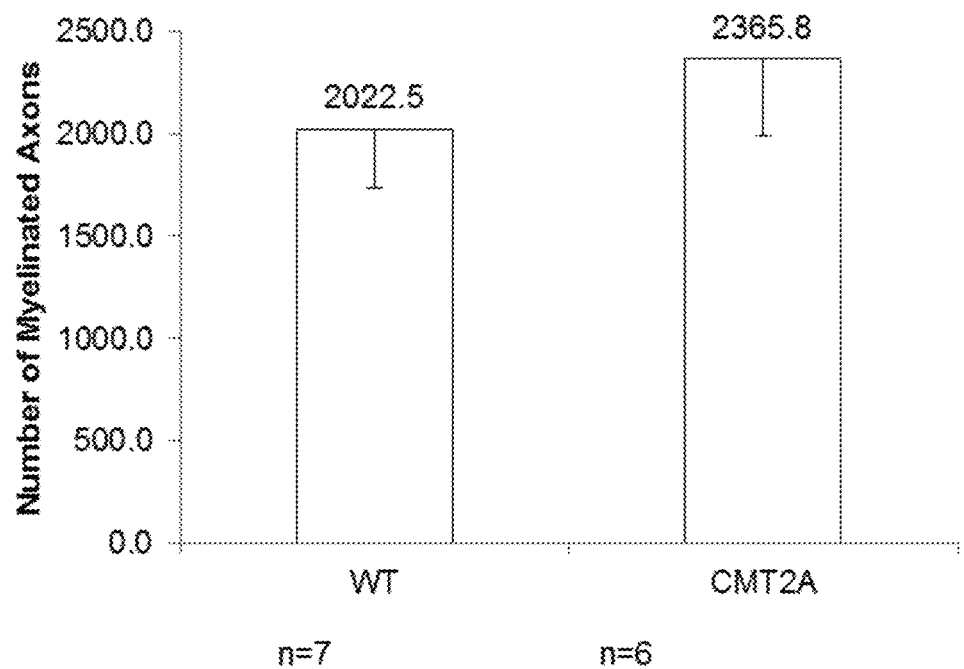

FIG. 6: Reduced numbers of myelinated axons in the distal tibial nerve, but not in the ventral roots, of R364W mutant rats.

The average number of myelinated axons in the tibial nerve (at the level of the ankle) and at the lumbar 5 ventral root in 48-week-old male rats heterozygous for the R364W mutation (CMT2A) was reduced by 84% compared to their age-matched, wild type (WT) male littermates. The number of animals per group is indicated below the bars. Error bars represent SD.

Figure 7:
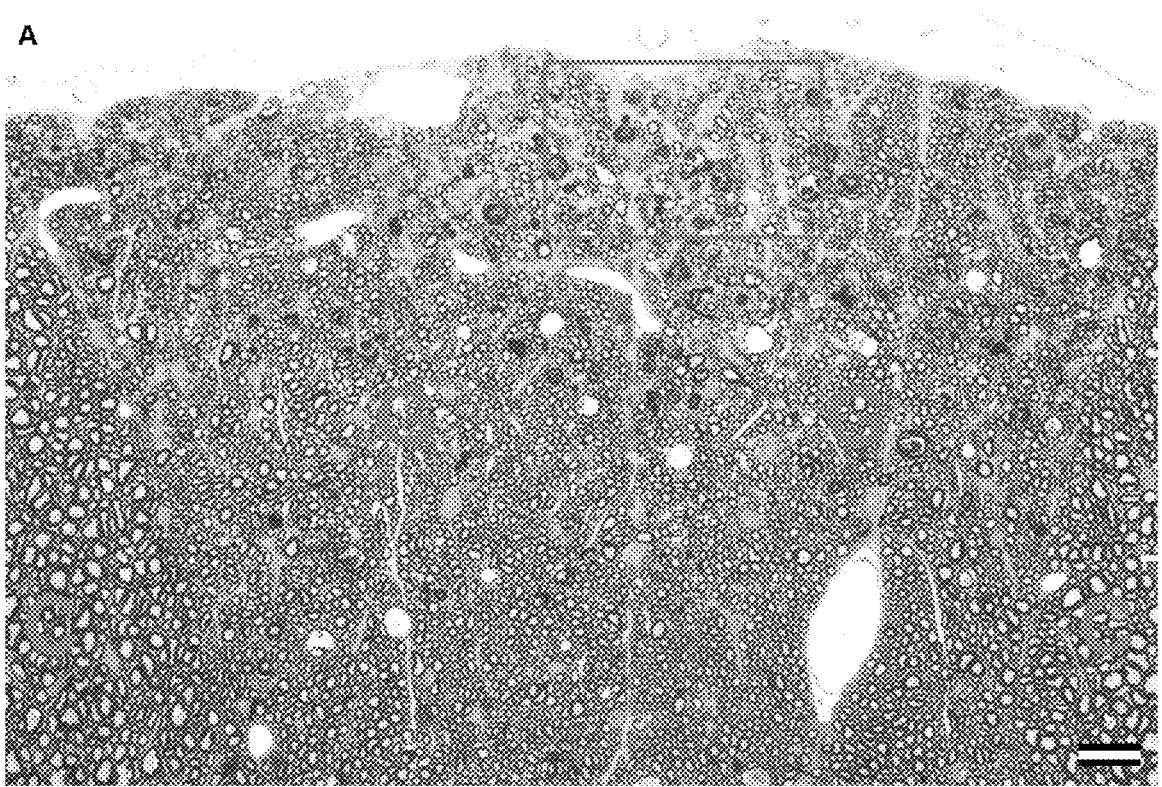
Figure 7:
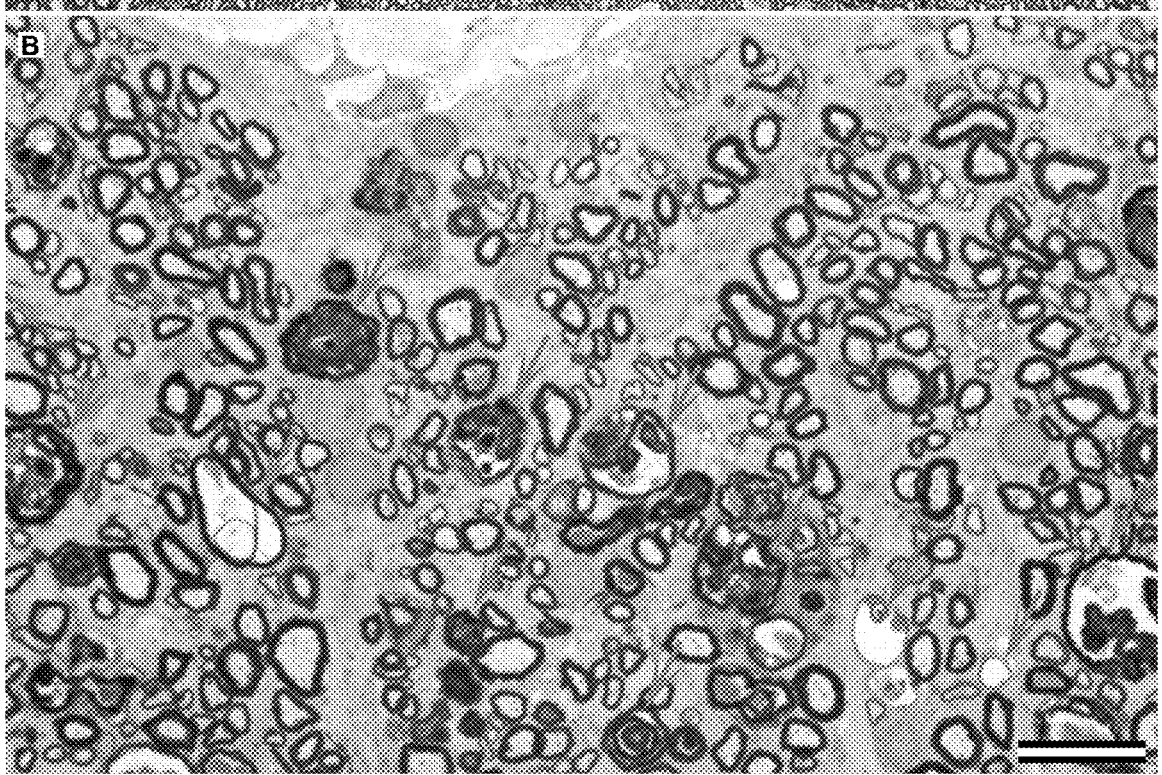

FIG. 7: Pathological findings in the cervical spinal cord of R364W mutant rats. These are images of a semi-thin section of the cervical spinal cord from a 40-week-old male rat heterozygous (HET) for the R364W mutation. Panel (A) shows the fasciculus gracilis (G) and cuneatus (C); the midline is indicated by a dotted line, and the region of the rectangle is shown in panel (B). Note the degenerating myelinated axons (arrows), which are mostly found in the superficial aspect of the fasciculus gracilis. Scale bar: A, 20 microns; B, 100 microns.

Figure 8:
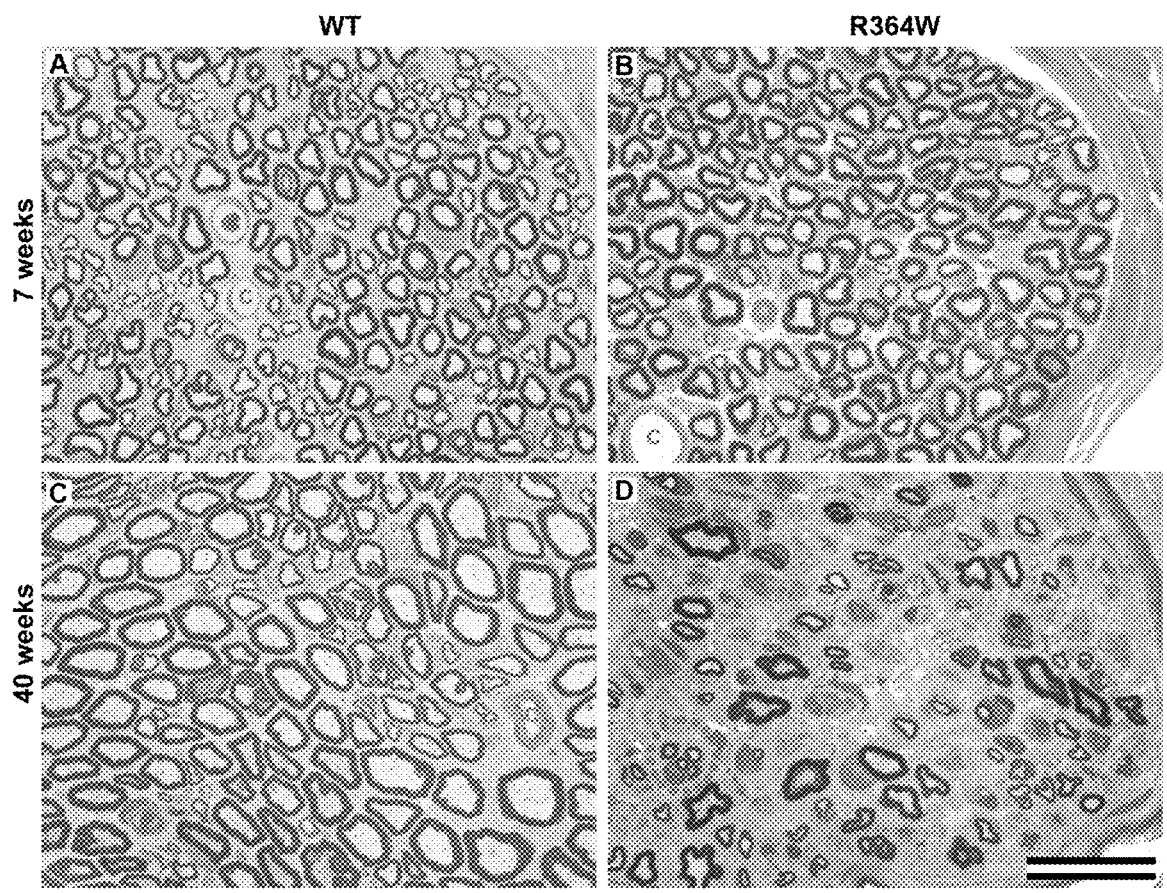

FIG. 8: Pathological findings in sural nerves of R364W mutant rats. These are images of semi-thin sections of the sural nerve from 7-week-old (A, B) and 40-week-old (C, D) rats. Panels (A) and (B), from a 7-week-old wild-type male rat and from male rats heterozygous for the R364W mutation, respectively, show no apparent pathology. Compared to a 40-week-old WT rat (C), the 40-week-old R364W mutant rat (D) show several pathological features: the density of myelinated axons is reduced; actively degenerating myelinated axons (arrows) and clusters of regenerating axons (dotted circles) are found in the endoneurium. C: capillary. Scale bar: 100 microns.

Figure 9:
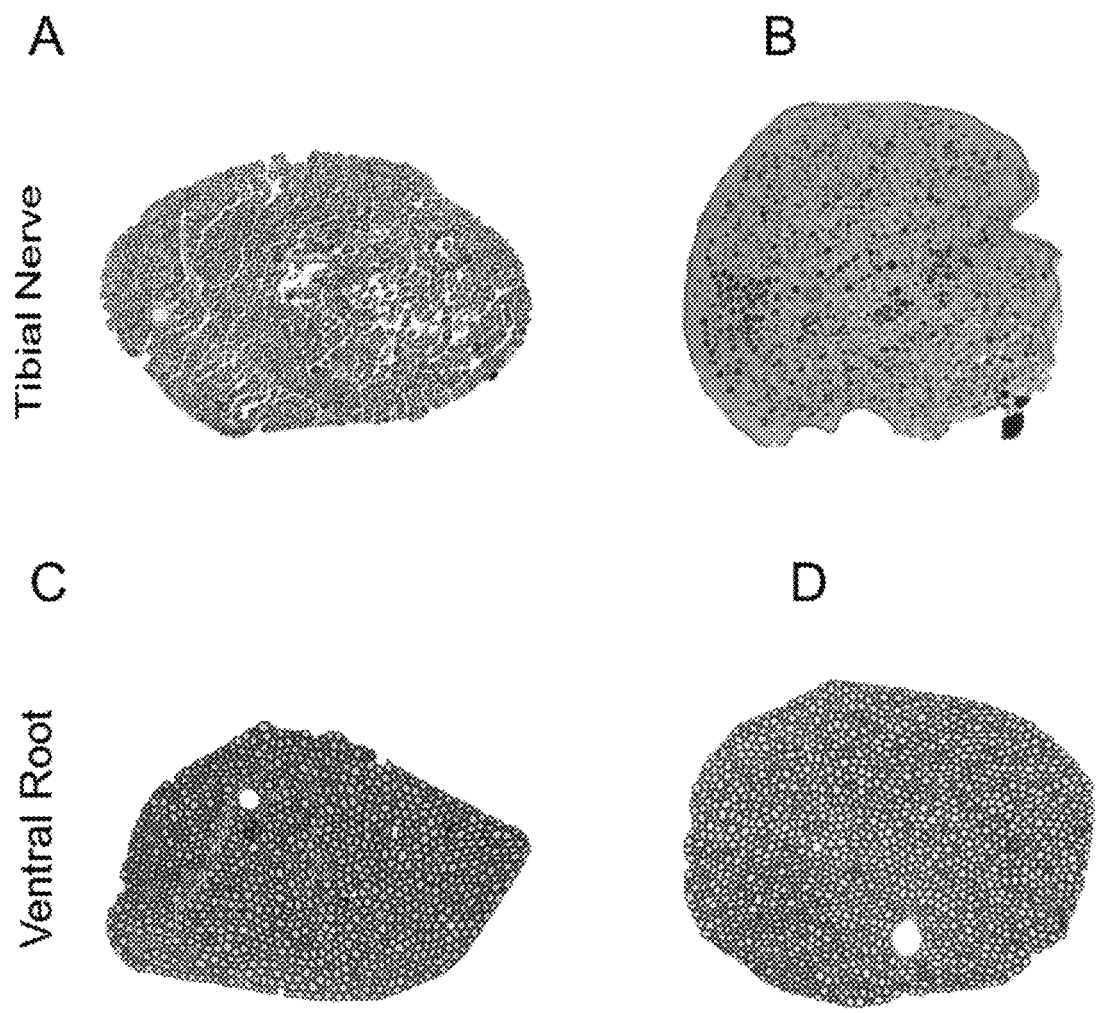

FIG. 9: Reduced numbers of myelinated axons in the distal tibial nerve, but not in the ventral roots, of R364W mutant rats.

These are images of a semi-thin section, stained with para-phenylenediamine, of the tibial nerve (at the ankle) and an L5 ventral root from an 11-month-old male rat heterozygous for the R364W mutation rat and a male wildtype littermate. The density of myelinated axons is clearly reduced in the tibial nerve of the mutant rat (A) compared to wildtype (B), but not in the L5 ventral root comparison of mutant and wildtype rat (C, D). Scale bar: 100 μm.

Figure 10:
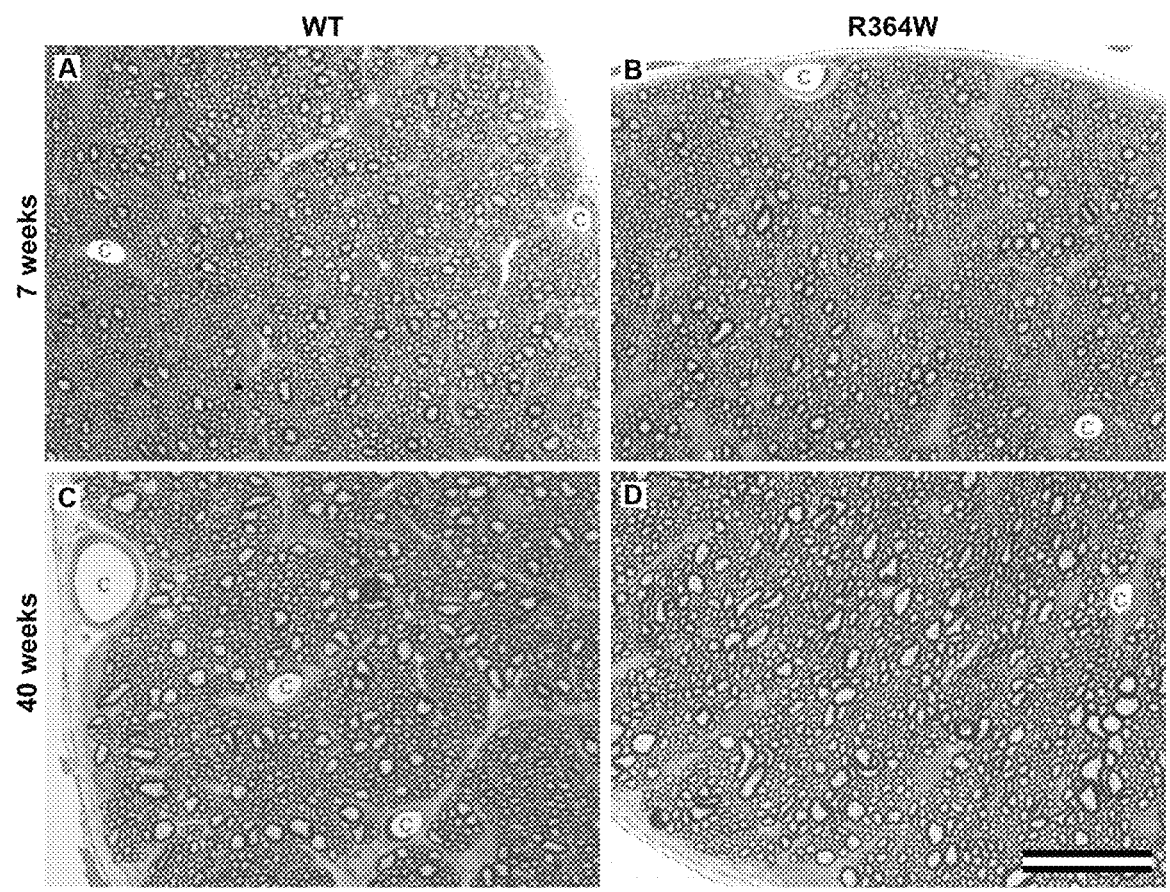

FIG. 10: No pathological findings in optic nerves of R364W mutant rats.

These are images of semi-thin sections of the optic nerve from 7-week-old (A, B) and 40-week-old (C, D) male rats heterozygous for the R364W mutation (R364W) and male wildtype (WT) rats, as indicated. There are no pathological findings in any specimen. C: capillary. Scale bar: 100 microns.

Figure 11:
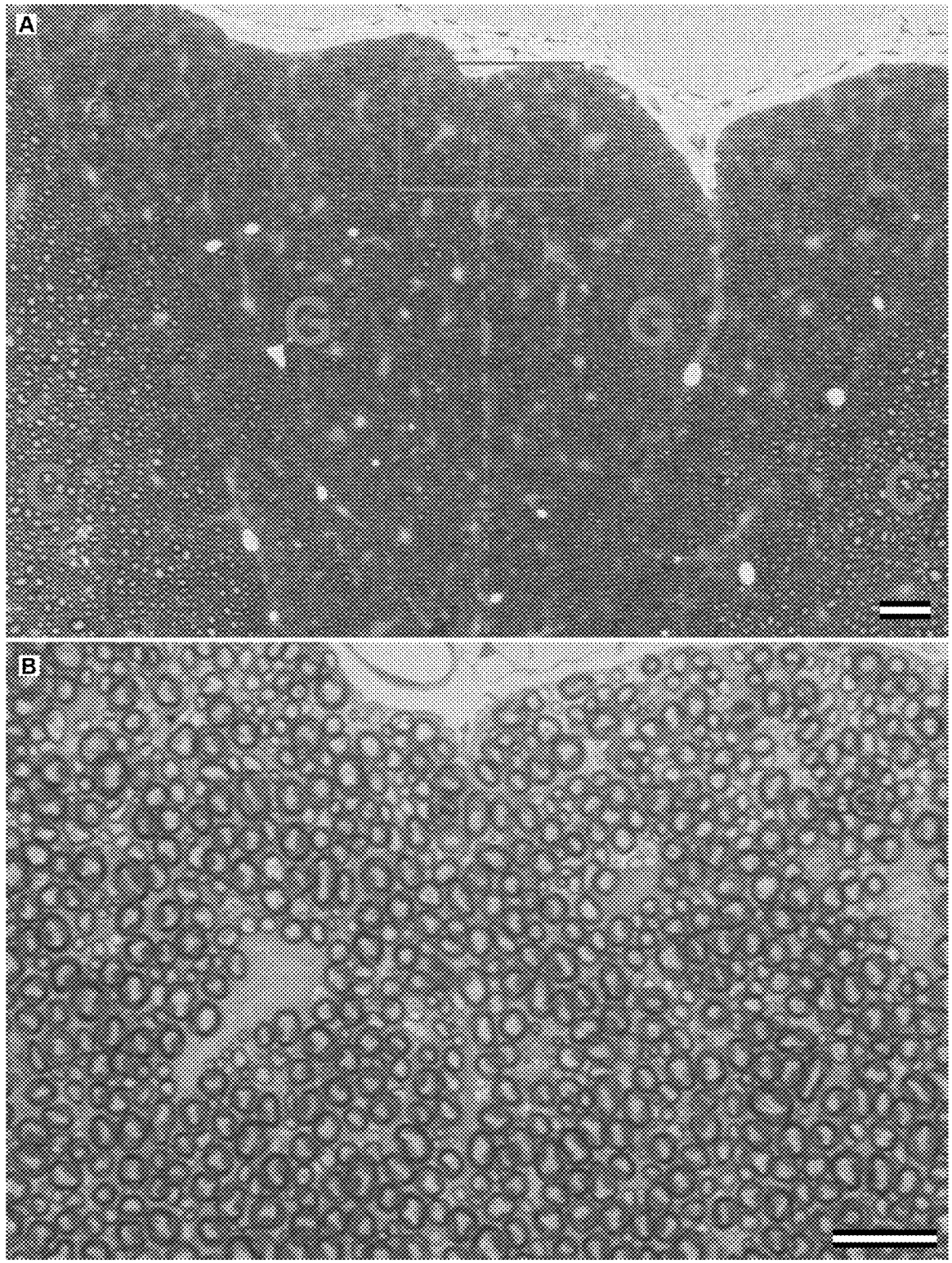

FIG. 11: No axonal degeneration in the 7-week-old R364W rats.

These are images of semi-thin sections of a cervical spinal cord from a 7-week-old R364W rat. Panel (A) shows the fasciculus gracilis (G) and cuneatus (C); the midline is indicated by a dotted line, and the region of the rectangle is shown in panel (B). There are no pathological findings. Scale bar: A, 20 microns; B, 100 microns.

Figure 12:
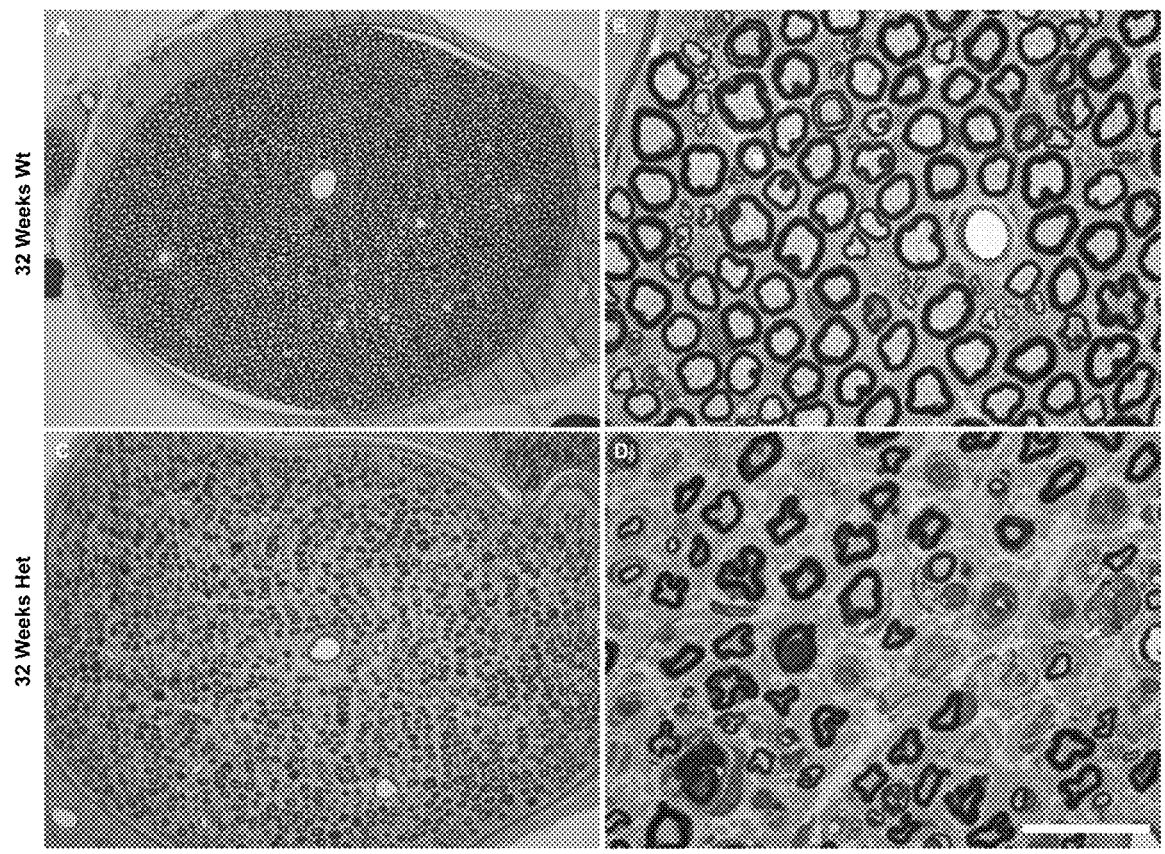

FIG. 12: Pathological findings in sural nerves of H361Y mutant rats. These are images of semi-thin sections of the distal tibial nerve from 32-week-old wild type male rats (A, B) and male rats heterozygous for the H361Y mutation (C, D). Panels (A) and (B) show no apparent pathology. The 32-week-old H361Y mutant rat (C, D) shows several pathological features—reduced density of myelinated axons (compare A to C), and actively degenerating myelinated axons (arrow and arrowhead) in (D). Scale bar: 50 microns applies to panels B and D.

DETAILED SUMMARY OF THE INVENTION

The present invention may be understood more readily by reference to the following detailed description of preferred embodiments of the invention and the examples included therein and to the Figures and their description. Although any methods and materials similar or equivalent to those described herein can be used in the practice or testing of the present invention, the preferred methods, devices, materials are now described. All references, publications, patents, patent applications, and commercial materials mentioned are incorporated herein by reference for the purpose of describing and disclosing the materials and/or methodologies which are reported in the publications which might be used in connection with the invention.

It is to be understood that this invention is not limited to specific synthetic methods, specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise.

Ranges may be expressed herein as from "about" on particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In this specification and in the claims which follow, reference will be made to a number of terms which shall be defined to have the following meanings:

A "coding sequence" of a sequence "encoding" an expression product, such as RNA, polypeptide protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme, A coding sequence for a protein may include a start codon (usually ATG) and a stop codon.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed". An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "gene", also called a "structural gene" means a DNA sequence that codes for or corresponds to a particular sequence of amino acids which comprise all or part of one or more proteins or enzymes, and may or may not include introns and regulatory DNA sequences, such as promoter sequences, 5'-untranslated region, or 3'-untranslated region which affect for example the conditions under which the gene is expressed. Some genes, which are not structural genes, may be transcribed from DNA to RNA, but are not translated into an amino acid sequence. Other genes may function as regulators of structural genes or as regulators of DNA transcription.

By "genetically modified or altered" is meant a gene that is altered from its native state (e.g. by insertion mutation, deletion mutation, nucleic acid sequence mutation, or other mutation), or that a gene product is altered from its natural state (e.g. by delivery of a transgene that works in trans on a gene's encoded mRNA or protein, such as delivery of inhibitory RNA or delivery of a dominant negative transgene).

The term "insertional mutation" is used herein to refer the translocation of nucleic acid from one location to another location which is in the genome of an animal so that it is integrated into the genome, thereby creating a mutation in the genome. Insertional mutations can also include knocking out or knocking in of endogenous or exogenous DNA via gene trap or cassette insertion. Exogenous DNA can access the cell via electroporation or chemical transformation. If the exogenous DNA has homology with chromosomal DNA it will align itself with endogenous DNA. The exogenous DNA is then inserted or disrupts the endogenous DNA via two adjacent crossing over events, known as homologous recombination. A targeting vector can use homologous recombination for insertional mutagenesis. Insertional mutagenesis of endogenous or exogenous DNA can also be carried out via DNA transposon. The DNA transposon is a mobile element that can insert itself along with additional exogenous DNA into the genome. Insertional mutagenesis of endogenous or exogenous DNA can be carried out by retroviruses. Retroviruses have a RNA viral genome that is converted into DNA by reverse transcriptase in the cytoplasm of the infected cell. Linear retroviral DNA is transported into the nucleus, and become integrated by an enzyme called integrase. Insertional mutagenesis of endogenous or exogenous DNA can also be done by retrotransposons in which an RNA intermediate is translated into DNA by reverse transcriptase, and then inserted into the genome.

By "knock-in" refers to a genetic engineering method that involves the one-for-one substitution of DNA sequence information with a wild-type copy in a genetic locus or the insertion of sequence information not found within the locus.

A "mutation" is a detectable change in the genetic material in the animal, which is transmitted to the animal's progeny. A mutation is usually a change in one or more deoxyribonucleotides, the modification being obtained by, for example, adding, deleting, inverting, or substituting nucleotides. Exemplary mutations include but are not limited to a deletion mutation, an insertion mutation, a nonsense mutation or a missense mutation.

Thus, the terms "mutation" or "mutated" as used herein are intended to denote an alteration in the "normal" or "wild-type" nucleotide sequence of any nucleotide sequence or region of the allele. As used herein, the terms "normal" and "wild-type" are intended to be synonymous, and to denote any nucleotide sequence typically found in nature. The terms "mutated" and "normal" are thus defined relative to one another; where a cell has two chromosomal alleles of a gene that differ in nucleotide sequence, at least one of these alleles is a "mutant" allele as that term is used herein. Based on these definitions, an "endogenous toxicology gene" is the "wild-type" gene that exists normally in a cell, and a "mutated toxicology gene" defines a gene that differs in nucleotide sequence from the wild-type gene.

"Nucleic Acid sequence mutation" is a mutation to the DNA of a gene that involves change of one or multiple nucleotides. A point mutation which affects a single nucleotide can result in a transition (purine to purine or pyrimidine to pyrimidine) or a transversion (purine to pyrimidine or pyrimidine to purine). A point mutation that changes a codon to represent a different amino acid is a missense mutation. Some point mutations can cause a change in amino acid so that there is a premature stop codon; these mutations are called nonsense mutations. A mutation that inserts or deletes a single base will change the entire downstream sequence and are known as frameshift mutations. Some mutations change a base pair but have no effect on amino acid representation; these are called silent mutations. Mutations to the nucleic acid of a gene can have different consequences based on their location (intron, exon, regulatory sequence, and splice joint).

As used herein, the term "phenotype" means any property of a cell or organism. A phenotype can simply be a change in expression of an mRNA or protein. Examples of phenotypes also include, but are in no way limited to, cellular, biochemical, histological, behavioral, or whole organismal properties that can be detected by the artisan. Phenotypes include, but are not limited to, cellular transformation, cell migration, cell morphology, cell activation, resistance or sensitivity to drugs or chemicals, resistance or sensitivity to pathogenic protein localization within the cell (e.g. translocation of a protein from the cytoplasm to the nucleus), resistance or sensitivity to ionizing radiation, profile of secreted or cell surface proteins, (e.g., bacterial or viral) infection, post-translational modifications, protein localization within the cell (e.g. translocation of a protein from the cytoplasm to the nucleus), profile of secreted or cell surface proteins, cell proliferation, signal transduction, metabolic defects or enhancements, transcriptional activity, recombination intermediate joining, DNA damage response, cell or organ transcript profiles (e.g., as detected using gene chips), apoptosis resistance or sensitivity, animal behavior, organ histology, blood chemistry, biochemical activities, gross morphological properties, life span, tumor susceptibility, weight, height/length, immune function, organ function, any disease state, and other properties known in the art. In certain situations and therefore in certain embodiments of the invention, the effects of mutation of one or more genes in a cell or organism can be determined by observing a change in one or more given phenotypes (e.g., in one or more given structural or functional features such as one or more of the phenotypes indicated above) of the mutated cell or organism compared to the same structural or functional feature(s) in a corresponding wild-type or (non-mutated) cell or organism (e.g., a cell or organism in which the gene(s) have not been mutated).

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease Si), as well as protein binding domains (consensus sequences) responsible for the binding of RNA polymerase. The promoter may be operatively associated with other expression control sequences, including enhancer and repressor sequences.

For the purposes of the present invention, the term "zinc finger nuclease" or "ZFN" refers to a chimeric protein molecule comprising at least one zinc finger DNA binding domain effectively linked to at least one nuclease or part of a nuclease capable of cleaving DNA when fully assembled. Ordinarily, cleavage by a ZFN at a target locus results in a double stranded break (DSB) at that locus.

The Model

The present invention provides two desired rat models which contains predefined, specific and desired alterations which causes the severe, early-onset axonal neuropathy, as well as myelopathy and optic atrophy phenotype in humans, characteristic of CMT2A. Specifically, the invention pertains to a genetically altered rat having a length-dependent axonal neuropathy characteristic of CMT2A in the peripheral nerves and in the fasciculus gracilis which appear after 7 weeks of age.

In one embodiment, the genetically altered animal is a rat and is able to serve as a useful model for CMT2A in humans, assessing therapeutics, drug screening or diagnosis. The invention additionally pertains to the use of such rats and their progeny in research and medicine.

Generating p.Arg364Trp (R364W) and p.His361Tyr (H361Y) Mutant Rats

For the R364W mutation, genome editing was performed with zinc finger nuclease to incorporate the desired mutation. Two custom zinc finger nucleases were designed to the target exon 10 of the rat Mfn2 gene (Seq ID 1).

A donor vector was designed to introduce the R364W mutation by converting CGG to the TGG codon (Arg to Trp). In addition, the A365 codon was altered to introduce a silent mutation (GCT) to create a Dde1 restriction site, forming the construct (Seq ID 2). Zinc finger nucleases and recombination donor were microinjected into one-cell stage rat embryos harvested from wild type female Sprague-Dawley rats. One founder was identified in the first eight animals that were screened, and was bred with Sprague-Dawley rats. Heterozygous rats were genotyped by PCR, using the following pair of primers (Seq ID 3) and (Seq ID 4). PCR products were digested with DdeI.

Generation of the H361Y mutant was accomplished using the genome editing tool CRISPR/Cas9 by co-injecting with an oligo donor containing the following mutation (Seq ID 5) converting the CAC codon in the target exon 10 of the rat Mfn2 gene to TAT (His to Tyr) with the silent mutation GTG to introduce a restriction site for AccI. Genotyping by PCR was accomplished using the following pair of primers (Seq ID 6) and (Seq ID 7).

Table 1 shows the nucleotide sequence and primer sequences for the generation of R364W and H351Y.

TABLE 1

| Sequence ID Number | Peptide Sequence | Sequence Identification |
|---|---|---|
| 1 | GAGTG CATTT CCCAG TCTGC AGTAA AGACC AAATT TGAGC AGCAC ACAGT CCGGG CCAAG CAGAT TGCAG AGGCC GTCCG TCTCA TCATG GATTC CCTGC ACATT GCGGC TCAGG AGCAG CG | Exon 10 of rat Mfn2 gene |
| 2 | GAGTG CATTT CCCAG TCTGC AGTAA AGACC AAATT TGAGC AGCAC ACAGT CTGGG CTAAG CAGAT TGCAG AGGCC GTCCG TCTCA TCATG GATTC CCTGC ACATT GCGGC TCAGG AGCAG CG | R354W |
| 3 | CGAGA GGCGA TTTGA GGTAA | F. Primer |
| 4 | CTGAC CAGTG TGACC AGGTG | R. Primer |
| 5 | GAGTG CATTT CCCAG TCTGC AGTAA AGACC AAATT TGAGC AGTAT ACAGT GCGGG CCAAG CAGAT TGCAG AGGCC GTCCG TCTCA TCATG GATTC CCTGC ACATT GCGGC TCAGG AGCAG CG | H361Y |
| 6 | CGAGA GGCGA TTTGA GGTAA | F. Primer |
| 7 | CTGAC CAGTG GACCA GGTG | R. Primer |

Phenotyping/Behavioral Testing

A cohort of 20 p.R364W mutants and 20 wild-type littermates were bred on a Sprague-Dawley background, and maintained in a 12/12 h light/dark cycle at 22±1° C. and a relative humidity approximately 50%. Food and water was provided ad libitum. All animals were examined, handled and weighed prior to initiation of the study to assure adequate health and to minimize the non-specific stress associated with testing. The experiments were conducted during the animal's light cycle phase.

Sensory impairment was assessed by the hotplate plate test (Ankier, S. I., 1974. New hot plate tests to quantify antinociceptive and narcotic antagonist activities. Eur. J. Pharmacol. 27, 1-4). Gross deficits in motoric activity were assessed using the rotarod test (Jones, B. J., Roberts, D. J., 1968. The quantitative measurement of motor incoordination in naive mice was made using an accelerating rotarod. J. Pharm. Pharmacol. 20, 302-304) and by employing the tapered balance beam test (Strome, E. M., Cepeda, I. L., Sossi, V., Doudet, D. J., 2006. Evaluation of the integrity of the dopamine system in a rodent model of Parkinson's disease: small animal positron emission tomography compared to behavioral assessment and autoradiography. Mol Imaging Biol 8, 292-299; Schallert, T., Woodlee, M. T., 2005. Orienting and Placing, in: Whishaw, I. Q., Kolb, B. (Eds.), The Behavior of Laboratory Rat: A Handbook with Tests. Oxford University Press, New York, pp. 129-140). For grip strength measurement (Meyer, O. A., Tilson, H. A., Byrd, W. C., Riley, M. T., 1979. A method for the routine assessment of fore- and hindlimb grip strength of rats and mice. Neurobiobehavioral Toxicology 1, 233-236), rats were acclimated in the test room for 1 hour, then held by the tail and lowered towards the mesh grip piece on a push-pull gauge (San Diego Instruments, San Diego, CA) until the animal grabbed the mesh grip piece with both fore limbs. The animal was then gently pulled backwards with consistent force until it released its grip. The forelimb grip force was recorded on the strain gauge. The animal was gently pulled backwards along the platform until the animal's hind paws grabbed the mesh grip piece on the push-pull gauge and then released its grip. The hind limb grip force was recorded on the strain gauge. Five consecutive grip trials separated by 1 min were recorded. The horizontal ladder test (Metz, G. A., Whishaw, I. Q., 2002, Cortical and subcortical lesions impair skilled walking in the ladder rung walking test: a new task to evaluate fore- and hindlimb stepping, placing, and co-ordination. J. Neurosci. Meth. 115, 169-179) assesses subtle motor coordination effects, as it requires fine dexterity in the paws in order to grip rungs of the ladder during locomotion. Coordinated movement and fine motor control was examined by placing the rat in a clear plexiglass chamber 1 meter long consisting of a walkway of irregularly spaced metal rungs over which the animal must traverse to reach a goal box. A 60 W lamp was placed at the start of the horizontal ladder to encourage the animal to traverse to the opposite end where a dark goal box is located. For each test session, the animals were allowed to walk over the ladder and foot fall errors were counted. The test was videotaped and foot errors were scored by a trained observer. The NeuroCube® System (Alexandrov, V., Brunner, D., Hanania, T., Leahy, E., 2015. High-throughput analysis of behavior for drug discovery. Eur J Pharmacol 750, 82-89) employs computer vision to detect changes in gait geometry and gait dynamics in rodents. Rats were placed in the NeuroCube® System for a 5 min test. The most dominant of the features that separate wildtype from mutant rats were identified and ranked. Bioinformatic algorithms were employed to calculate the discrimination probability between wildtype and mutant rats. The outcomes differentiate a set of features that include: average speed; body position; gait; paw positioning; paw contact imaging and relative limb movement (rhythmicity).

Data were analyzed by Student's unpaired t-test or repeated-measured analysis of variance (ANOVA), followed by post-hoc comparisons when appropriate. An effect was considered significant if $p<0.05$.

Histology

Separate cohorts of male R364W mutant rats and their wild-type male littermates were analyzed by histology at 7 (5 mutant and 2 wild-type), 40 (4 mutants and 4 wild-type), and 48 (8 mutants and 7 wild-type) weeks of age. The rats were euthanized with an intraperitoneal injection of ketamine (200 mg/kg) and xylazine (10 mg/kg), then transcardially perfused with 50 ml of 0.9% NaCl followed by 300 ml of 2% paraformaldehyde and 2% glutaraldehyde in 0.1 M phosphate buffer (PB; pH=7.4). The sciatic nerves, femoral motor and sensory nerves, cervical spinal cords, and optic nerves were dissected and fixed for 3 hours, then rinsed in 0.1 M PB, transferred to a 2% OsO4 in 0.1 M PB, for 1 hour, then processed for embedding in Epon (Potter, K. A., Kern, M. J., Fullbright, G., Bielawski, J., Scherer, S. S., Yum, S. W., Li, J., Cheng, H., Han, X., Venkata, J. K., Khan, P. A. A., Rohrer, B., Hama, H., 2011. Central nervous system dysfunction in a mouse model of FA2H deficiency. Glia 59, 1009-1021). Semi-thin sections were stained with alkaline toluidine blue, and visualized by light microscopy (Leica DMR) using interactive software (Leica Application Suite). Selected images were processed with Photoshop to generate the figures.

The rats were perfused with fixative containing 2.5% glutaraldehyde and 4% paraformaldehyde. Peripheral nerves from the animals were carefully dissected, post-fixed for 90 mins in 0.4% osmium tetroxide, dehydrated through graded ethanol, washed in propylene oxide, and embedded in Epon-812 resin (Electron Microscopy Sciences). One micron thick transverse sections were stained for 3 mins in 1% aqueous para-phenylenediamine, rinsed with 100% ethanol and mounted. Sections were scanned in a Mirax slide scanner equipped with a 20×objective (Zeiss). Images were imported into NIH ImageJ/Fiji software (Schindelin, J., Arganda-Carreras, I., Frise, E., Kaynig, V., Longair, M., Pietzsch, T., Preibisch, S., Rueden, C., Saalfeld, S., Schmid, B., Tinevez, J. Y., White, D. J., Hartenstein, V., Eliceiri, K., Tomancak, P., Cardona, A., 2012. Fiji: an open-source platform for biological-image analysis. Nat Methods 9, 676-682), ImageJ v 1.48s, Java1.6.0 24 (64 bit). Myelinated axons were counted using automated thresholding and the ImageJ built-in particle analysis feature. False positive elimination was performed based on size and circularity criteria, and 10% of the samples were validated manually by an expert rater. Data were compared by t-tests, using the GraphPad Prism statistical package.

Results—Generating Mutant Rats

Figure 1:
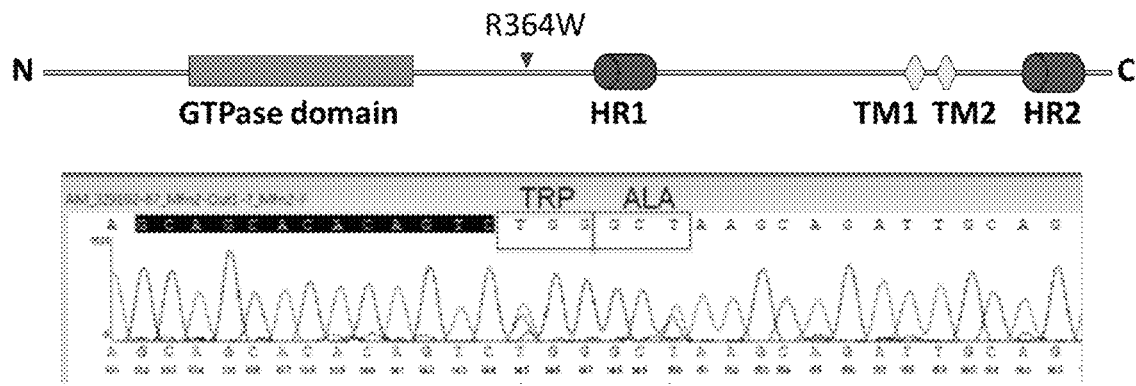
FIG. 1: Generating a p.Arg364Trp (R364W) mutant rat.

For R364W mutant rats zinc finger nuclease technology was used to generate the respective knock-in mutation in rats. FIG. 1 shows a diagram indicating the functional domains of Mitofusin 2 protein along with the relative position of the R364W mutation. The R364W human mutation was selected because it results in a severe early-onset axonal neuropathy, with 8 different affected families of several ethnic origins (Züchner, S., Mersiyanova, I. V., Muglia, M., Bissar-Tadmouri, N., Rochelle, J., Dadali, E. L., Zappia, M., Nelis, E., Patitucci, A., Senderek, J., Parman, Y., Evgrafov, O., de Jonghe, P., Takahashi, Y., Tsuji, S., Pericak-Vance, M. A., Quattrone, A., Battologlu, E., Polyakov, A. V., Timmerman, V., Schroder, J. M., Vance, J. M., 2004. Mutations in the mitochondrial GTPase mitofusin 2 cause Charcot-Marie-Tooth neuropathy type 2A. Nat Genet 36, 449-451; Chung, K. W., Kim, S. B., Park, K. D., Choi, K. G., Lee, J. H., Eun, H. W., Suh, J. S., Hwang, J. H., Kim, W. K., Seo, B. C., Kim, S. H., Son, I. H., Kim, S. M., Sunwoo, I. N., Choi, B. O., 2006. Early onset severe and late-onset mild Charcot-Marie-Tooth disease with mitofusin 2 (MFN2) mutations. Brain 129, 2103-2118; Feely, S. M. E., Laura, M., Siskind, C. E., Sottile, S., Davis, M., Gibbons, V. S., Reilly, M. M., Shy, M. E., 2011. MFN2 mutations cause severe phenotypes in most patients with CMT2A. Neurology 76, 1690-1696; Lin, K. P., Soong, B. W., Yang, C. C., Huang, L. W., Chang, M. H., Lee, I. H., Antonellis, A., Lee, Y. C., 2011. The mutational spectrum in a cohort of Charcot-Marie-Tooth disease type 2 among the Han Chinese in Taiwan. PLoS One 6, e29393; Sitarz, K. S., Yu-Wai-Man, P., Pyle, A., Stewart, J. D., Rautenstrauss, B., Seeman, P., Reilly, M. M., Horvath, R., Chinnery, P. F., 2012. MFN2 mutations cause compensatory mitochondrial DNA proliferation. Brain 135, e219, 211-213; author reply e220, 211-213; Bombelli, F., Stojkovic, T., Dubourg, O., Echaniz-Laguna, A., Tardieu, S., Larcher, K., Amati-Bonneau, P., Latour, P., Vignal, O., Cazeneuve, C., Brice, A., Leguern, E., 2014. Charcot-Marie-Tooth disease type 2A: from typical to rare phenotypic and genotypic features. JAMA neurology 71, 1036-1042). One founder was identified in the first eight rats that were screened, and was bred in a Sprague-Dawley background.

The genome editing tool CRISPR/Cas9 was used to target rat Mfn2 by co-injecting with an oligo donor containing a H361Y mutation. The co-injected oligo donor contained the following mutation TATACAGTGCGGGCCAAGCAGAT-TGCAGAGGCC (Seq ID 5) converting the CAC codon in the target exon 10 of the rat Mfn2 gene to TAT (His to Tyr) with the silent mutation GTG to introduce a restriction site for AccI. Genotyping by PCR was accomplished using the following pair of primers: CeliF: 5'-CGAGAGGCGATTT-GAGGTAA (Seq ID 6) and CeliR: 5'-CTGACCAGTGTGACCAGGTG (Seq ID 7). After PCR reaction using CellF and CellR as the primer set, the PCR product was digested with AccI enzyme (NEB) for 1 hour at 37° C. The product was resolved on a 3% agarose gel or 10% TBE polyacrylamide gel. Further verification was obtained by purifying the PCR product and sequencing.

Results—Behavioral Analysis

We examined a cohort of R364W Mfn2 mutant male rats (n=20) and their wild type male littermates (n=20). We used male rats to maintain consistent, average body weight between groups, and to avoid inclusion of variable, gender-specific test responses. We found no significant differences between the groups in gross motoric deficits as assessed using the rotarod and tapered balance beam tests from 7 weeks to one year of age (data not shown). The hotplate test, an assay of thermal nociception, also failed to show significant differences between the groups. Mfn2 mutant rats had weaker forelimb and hindlimb grip strength compared to their wild type male littermates at 7, 13, and 19 weeks (individual t-test analysis); at 25 (FIG. 2) and 52 (data not shown) weeks, there was no significant genotype effect in either measure. Repeated measures ANOVA also showed that Mfn2 mutant rats were significantly weaker in both forelimb and hindlimb grip strength compared to than their wild type littermates. The horizontal ladder test, used to assess deficits in fine motor coordination while navigating a horizontal ladder with irregularly spaced rungs, also revealed significantly more hindlimb footfalls in Mfn2 mutant male rats compared to their wild type male littermates at 30 and 52 weeks (FIG. 3). Forelimb footfalls were not significantly affected at either age (data not shown).

Gait abnormalities were assessed using the automated NeuroCube® System (Alexandrov, V., Brunner, D., Hanania, T., Leahy, E., 2015. High-throughput analysis of behavior for drug discovery. Eur J Pharmacol 750, 82-89) for R364W mutant male rats between 7 and 52 weeks of age.

Mfn2 mutant male rats showed significant deficits in gait (both gait geometry and dynamics) compared to their wild type male littermates at all ages tested (Table 1). A progressive increase in paw positioning and in paw contact imaging was also observed in the R364W mutant male rats at weeks 7, 15, and 19. A shorter stance duration, together with a longer swing duration, suggested an unstable gait, while increased step length and base width further suggested that they had a splayed gait (data not shown). In addition, R364W HET male rats showed decreases in most of the gait measures shown in Table 1, including average speed, relative limb movement (rhythmicity), and body motion. These effects were particularly apparent at weeks 13 and 19 of age. At one year of age, mutant male rats showed strong deficits in all of the measures shown in Table 2.

TABLE 2 p.R364W mutant rats have abnormal gait and body movement.

Discrimination between WT and HET rats

| Feature | Week 7 | | Week 13 | | Week 19 | | Week 26 | | Month 12 | |
|---|---|---|---|---|---|---|---|---|---|---|
| Gait | 84% | P = 0.001 | 84% | P = 0.002 | 87% | P = 0.005 | 95% | P = 0.005 | 89% | P = 0.002 |
| Average Speed | 52% | P = 0.66 | 58% | P = 0.47 | 60% | P = 0.42 | 62% | P = 0.38 | 91% | P < 0.001 |
| Rhythmicity | 55% | P = 0.47 | 58% | P = 0.42 | 62% | P = 0.45 | 64% | P = 0.36 | 63% | P = 0.037 |
| Paw Position | 71% | P = 0.039 | 85% | P < 0.001 | 98% | P < 0.001 | 68% | P = 0.26 | 90% | P = 0.001 |
| Body Motion | 62% | P = 0.14 | 82% | P < 0.001 | 67% | P < 0.67 | 67% | P = 0.29 | 84% | P = 0.001 |
| Imaging | 72% | P = 0.005 | 85% | P < 0.001 | 92% | P < 0.003 | 80% | P = 0.06 | 72% | P = 0.013 |

The automated NeuroCube® System was used to independently assess gait, as well as body and limb positioning. Male rats heterozygous (HET) for the R364W mutation were compared with their male wild type (WT) littermates. Ages at the time of testing are indicated. Group sizes for week 30 were n=20, whereas the R364W mutant male group was n=18 at month 12. The results indicate a statistically significant differentiation between the two animal groups in gait for weeks 7 to 26, paw position for weeks 7 to 19, Body motion for week 13, imaging for week 7 to 19, and all features at 12 months.

For H361Y mutant rats, changes in gait dynamics were observed at week 8. CMT2A-H361Y HET rats showed abnormalities in gait dynamics. A shorter stand duration in both forelimbs and hindlimbs were detected. In addition, H361Y mutant animals showed increased base width of the forelimbs at 8 weeks although changes in hindlimb base width were not detected at this time point. The changes showing a faster gait cycle indicate earlier deficits in the forelimbs.

At 16 weeks, H361Y mutant rats showed further changes in gait dynamics. A shorter stand duration in both forelimbs and hindlimbs was detected similar to observations at 8 weeks. In addition, mutant animals showed increased step lengths and swing duration which indicate a lengthening of the gait cycle.

The abnormal gait and body movements between week 8 and week 16 are summarized in Table 3.

TABLE 3

H361YW mutant rats have abnormal gait and body movement

Discrimination between WT and HET rats

| Feature | Week 8 | | Week 16 | |
|---|---|---|---|---|
| Gait | 60% | P = 0.104 | 55% | P = 0.150 |
| Average Speed | 63% | P = 0.043 | 58% | P = 0.015 |
| Rhythmicity | 57% | P = 0.190 | 65% | P = 0.061 |
| Paw Position | 81% | P < 0.001 | 72% | P < 0.001 |
| Body Motion | 71% | P = 0.001 | 64% | P = 0.004 |
| Imaging | 55% | P = 0.399 | 56% | P < 0.001 |

The automated NeuroCube® System was used to independently assess gait, as well as body and limb positioning. Male heterozygous for the H361Y mutation (HET) were compared with their male wild type (WT) littermates. Ages at the time of testing are indicated. Group sizes were n=20. The results indicate a statistically significant differentiation between the two age groups in gait, body motion, and imaging at week 8 and 16.

Results—Pathological Analysis

To determine whether R364W mutant rats develop a peripheral neuropathy, we examined a cohort of 40-week-old mutant male rats (n=4) and their wild-type (n=4) male littermates. We prepared and analyzed semi-thin sections of selected peripheral nerves, the cervical spinal cord, and the optic nerves. Because peripheral neuropathy typically starts at the ends of the longest axons (length-dependent) and worsens over time (time-dependent), we examined the distal aspect of the sciatic nerve—the tibial (which contains motor and sensory axons) and the sural (which contains sensory axons) branches at the ankle. Compared to wild type rats (FIG. 4C), there was marked pathology in all of the tibial nerve samples from the mutant rats (FIG. 4D-F). The density of myelinated axons was reduced, there were degenerating myelinated axons, lipid-filled cells (either Schwann cells or macrophages), and clusters of regenerated axons. The sural nerves showed similar findings (FIG. 8). These findings demonstrate a distal axonal loss and regeneration in R364W mutant rats.

We also examined a more proximal nerve—the femoral motor and sensory branches (FIG. 5). Unlike the distal tibial nerve, degenerating myelinated axons and clusters of regenerated axons were not found in femoral motor and sensory branches of the mutant rats. The myelinated axons in the femoral sensory branch of mutants appeared normal (compare FIG. 5D to 5F). The most salient finding in the femoral motor branch was that many large (likely motor) myelinated axons in mutant rats had abnormally thin myelin sheaths (relative to their axonal caliber); one example is shown in FIG. 5C. Some of these thinly myelinated axons were partially surrounded by cellular processes (so-called "onion bulbs"). These histological findings strongly suggest that these axons have been remyelinated, which was unexpected because CMT2A is considered an "axonal" neuropathy (Verhoeven, K., Claeys, K. G., Züchner, S., Schroder, J. M., Weis, J., Ceuterick, C., Jordanova, A., Nelis, E., De Vriendt, E., Van Hul, M., Seeman, P., Mazanec, R., Saifi, G. M., Szigeti, K., Mancias, P., Butler, I. J., Kochanski, A., Ryniewicz, B., De Bleecker, J., Van den Bergh, P., Verellen, C., Van Coster, R., Goemans, N., Auer-Grumbach, M., Robberecht, W., Rasic, V. M., Nevo, Y., Tournev, I., Guergueltcheva, V., Roelens, F., Vieregge, P., Vinci, P., Moreno, M. T., Christen, H. J., Shy, M. E., Lupski, J. R., Vance, J. M., De Jonghe, P., Timmerman, V., 2006. MFN2 mutation distribution and genotype/phenotype correlation in Charcot-Marie-Tooth type 2. Brain 129, 2093-2102). The presence of remyelinated axons indicates that the R364W mutation has effects on myelinating Schwann cells that result in demyelination.

To confirm and extend these findings, we also examined the distal tibial nerves and an L5 ventral root from 11-month-old R364W mutant rats and their age-matched male littermates. As shown in FIG. 9 and summarized in FIG. 6, the number of myelinated axons was reduced by 84% in the distal tibial nerves but not in the L5 ventral root of R364W mutant rats compared to their age-matched male wildtype littermates. There was no significance difference between ventral root samples. Thus, the R364W mutation causes length-dependent axonal loss in this animal model.

Because some patients with the R364W mutation, as well as the R104W mutation, also have clinical findings of a myelopathy (Del Bo, R., Moggio, M., Rango, M., Bonato, S., DAngelo, M. G., Ghezzi, S., Airoldi, G., Bassi, M. T., Guglieri, M., Napoli, L., Lamperti, C., Corti, S., Federico, A., Bresolin, N., Comi, G. P., 2008. Mutated mitofusin 2 presents with intrafamilial variability and brain mitochondrial dysfunction. Neurology 71, 1959-1966; Chung, K. W., Suh, B. C., Cho, S. Y., Choi, S. K., Kang, S. H., Yoo, J. H., Hwang, J. Y., Choi, B. O., 2010. Early-onset Charcot-Marie-Tooth patients with mitofusin 2 mutations and brain involvement. J. Neurol. Neurosurg. Psychiat. 81, 1203-1206), we examined the cervical spinal cords. We found degenerating myelinated axons in the superficial/pial aspect of the fasciculus gracilis (FIG. 4); the other white matter tracts of the spinal cord were normal (data not shown). The axons of the superficial part of the fasciculus gracilis originate from the mechanoreceptors of the legs (Niu, J., Ding, L., Li, J. J., Kim, H., Liu, J., Li, H., Moberly, A., Badea, T. C., Duncan, I. D., Son, Y. J., Scherer, S. S., Luo, W., 2013. Modality-based organization of ascending somatosensory axons in the direct dorsal column pathway. J. Neurosci. 33, 17691-17709), and are thus the longest axons in the cervical spinal cord. It remains to be determined whether these axons are selectively affected because of their length, or because they are derived from sensory neurons.

Optic atrophy has been reported in CMT2A patients, including patients with the R364W mutation (Züchner, S., DeJonghe, P., Jordanova, A., Claeys, K. G., Guergueltcheva, V., Cheminkova, S., Hamilton, S. R., VanStavern, G., Krajewski, K. M., Stajich, J., Tournev, I., Verhoeven, K., Langerhorst, C. T., deVisser, M., Baas, F., Bird, T., Timmerman, V., Shy, M., Vance, J. M., 2006. Axonal neuropathy with optic atrophy is caused by mutations in mitofusin 2. Ann Neurol 59, 276-281; Chung, K. W., Kim, S. B., Park, K. D., Choi, K. G., Lee, J. H., Eun, H. W., Suh, J. S., Hwang, J. H., Kim, W. K., Seo, B. C., Kim, S. H., Son, I. H., Kim, S. M., Sunwoo, I. N., Choi, B. O., 2006. Early onset severe and late-onset mild Charcot-Marie-Tooth disease with mitofusin 2 (MFN2) mutations. Brain 129, 2103-2118; Feely, S. M. E., Laura, M., Siskind, C. E., Sottile, S., Davis, M., Gibbons, V. S., Reilly, M. M., Shy, M. E., 2011. MFN2 mutations cause severe phenotypes in most patients with CMT2A. Neurology 76, 1690-1696; Chung, K. W., Suh, B. C., Cho, S. Y., Choi, S. K., Kang, S. H., Yoo, J. H., Hwang, J. Y., Choi, B. O., 2010. Early-onset Charcot-Marie-Tooth patients with mitofusin 2 mutations and brain involvement. J. Neurol. Neurosurg. Psychiat. 81, 1203-1206). Therefore, we examined semi-thin sections of the optic nerves, but found no pathological changes at 40 weeks (FIG. 10).

To determine the onset of pathological changes, we examined a cohort of 7-week-old mutant (n=5) and wild type (n=2) rats. No pathological findings were seen in the distal tibial (FIG. 3), distal sural (FIG. 8), femoral motor (not shown), femoral sensory (not shown), and cervical spinal cords (FIG. 11) of 7-week-old R364W mutant rats or the wild type controls.

A similar delay in the onset of pathologic changes was observed in the H361Y mutant rats. FIG. 12 shows the pathological finding in sural nerves of the H361Y mutants. 32-week-old wild type (panel A and B) show no apparent pathology while 32-week-old heterozygous H361Y HET rat (panel C and D) shows several pathological features, including reduced density of myelinated axons (compare A to C), and actively degenerating myelinated axons (arrow and arrowhead) in (D).

DISCUSSION

The present invention provides genetically authentic animal models in both the R364W mutation and the H361Y mutant. These mutations cause a severe, early-onset axonal neuropathy, as well as myelopathy and optic atrophy phenotype in humans. These mutant rats develop a length-dependent axonal neuropathy in the peripheral nerves and in the fasciculus gracilis, both of which appear after 7 weeks of age. This model a valuable tool for examining the pathogenesis and treatment of CMT2A.

CMT2A Models.

Recessive models of Mfn2 mutations have been found in dogs (Fyfe, J. C., Al-Tamimi, R. A., Liu, J., Schaffer, A. A., Agarwala, R., Henthorn, P. S., 2011. A novel mitofusin 2 mutation causes canine fetal-onset neuroaxonal dystrophy. Neurogenetics 12, 223-232) and cows (Drogemuller, C., Reichart, U., Seuberlich, T., Oevermann, A., Baumgartner, M., Kuhni Boghenbor, K., Stoffel, M. H., Syring, C., Meylan, M., Muller, S., Muller, M., Gredler, B., Solkner, J., Leeb, T., 2011. An unusual splice defect in the Mfn2 gene is associated with degenerative axonopathy in Tyrolean Grey cattle. PLoS One 6, e18931), and have been generated in zebrafish (Chapman, A. L., Bennett, E. J., Ramesh, T. M., De Vos, K. J., Grierson, A. J., 2013. Axonal Transport Defects in a Mitofusin 2 Loss of Function Model of Charcot-Marie-Tooth Disease in Zebrafish. PLoS One 8, e67276) and mice (Chen, H. D. R., Detmer, S. A., Ewald, A. J., Griffin, E. E., Graser, S. E., Chan, D. C., 2003. Mitofusins Mfn1 and Mfn2 coordinately regulate mitochondrial fusion and are essential for embryonic development. J. Cell Biol. 160, 189-200). Except for the Mfn2-null mouse, which dies during embryogenesis, homozygous mutant animals develop a progressive neurological disease that affects axons; these may be appropriate animal models for homozygous and compound heterozygous-recessive Mfn2 mutations in humans, which typically cause a severe, early-onset axonal neuropathy (Verhoeven, K., Claeys, K. G., Züchner, S., Schroder, J. M., Weis, J., Ceuterick, C., Jordanova, A., Nelis, E., De Vriendt, E., Van Hul, M., Seeman, P., Mazanec, R., Saifi, G. M., Szigeti, K., Mancias, P., Butler, I. J., Kochanski, A., Ryniewicz, B., De Bleecker, J., Van den Bergh, P., Verellen, C., Van Coster, R., Goemans, N., Auer-Grumbach, M., Robberecht, W., Rasic, V. M., Nevo, Y., Tournev, I., Guergueltcheva, V., Roelens, F., Vieregge, P., Vinci, P., Moreno, M. T., Christen, H. J., Shy, M. E., Lupski, J. R., Vance, J. M., De Jonghe, P., Timmerman, V., 2006. MFN2 mutation distribution and genotype/phenotype correlation in Charcot-Marie-Tooth type 2. Brain 129, 2093-2102; Vallat, J. M., Ouvrier, R. A., Pollard, J. D., Magdelaine, C., Zhu, D., Nicholason, G. A., Grew, S., Ryan, M. M., Funalot, B., 2008. Histopathological findings in hereditary motor and sensory neuropathy of axonal type with onset in early childhood associated with Mitofusin 2 mutations. J Neuropathol Exp Neurol 67, 1097-1102; Nicholson, G. A., Magdelaine, C., Zhu, D., Grew, S., Ryan, M. M., Sturtz, F., Vallat, J. M., Ouvrier, R. A., 2008. Severe early-onset axonal neuropathy with homozygous and compound heterozygous MFN2 mutations. Neurology 70, 1678-1681; Polke, J. M., Laura, M., Pareyson, D., Taroni, F., Milani, M., Bergamin, G., Gibbons, V. S., Houlden, H., Chamley, S. C., Blake, J., Devile, C., Sandford, R., Sweeney, M. G., Davis, M. B., Reilly, M. M., 2011. Recessive axonal Charcot-Marie-Tooth disease due to compound heterozygous mitofusin 2 mutations. Neurology 77, 168-173). Conditionally deleting Mfn2 in selected neurons does produce a phenotype (Chen, H., McCaffery, J. M., Chan, D. C., 2007. Mitochondrial fusion protects against neurodegeneration in the cerebellum. Cell 130, 548-562; Pham, A. H., Meng, S., Chu, Q. N., Chan, D. C., 2012. Loss of Mfn2 results in progressive, retrograde degeneration of dopaminergic neurons in the nigrostriatal circuit. Hum Mol Genet 21, 4817-4826; Dietrich, M. O., Liu, Z. W., Horvath, T. L., 2013. Mitochondrial dynamics controlled by mitofusins regulate Agrp neuronal activity and diet-induced obesity. Cell 155, 188-199; Schneeberger, M., Dietrich, M. O., Sebastian, D., Imbernon, M., Castano, C., Garcia, A., Esteban, Y., Gonzalez-Franquesa, A., Rodriguez, I. C., Bortolozzi, A., Garcia-Roves, P. M., Gomis, R., Nogueiras, R., Horvath, T. L., Zorzano, A., Claret, M., 2013. Mitofusin 2 in POMC neurons connects ER stress with leptin resistance and energy imbalance. Cell 155, 172-187), although not necessarily an axonopathy.

One embodiment of the present invention is a R364W rat model which is the first dominant Mfn2 mutation that develops a robust neuropathy. Prior attempts to generate a CMT2A mouse model failed to produce a progressive axonal neuropathy. Detmer et al. expressed the p.T105 M mutation in motor neurons using the HB9 promoter (Detmer, S. A., Velde, C. V., Cleveland, D. W., Chan, D. C., 2008. Hindlimb gait defects due to motor axon loss and reduced distal muscles in a transgenic mouse model of Charcot-Marie-Tooth type 2A. Hum. Mol. Genet. 17, 367-375). Heterozygous, transgenic mice had a severe gait defect associated with reduced numbers of motor axons in the motor roots and severe reduction of the anterior calf muscles. There was evidence of progressive axonal degeneration, thus these deficits likely owe to a developmental loss of myelinated motor axons. Cartoni et al. generated two lines of transgenic mice expressing the p.R94Q mutation using a neuron-specific enolase promoter, and reported that heterozygous mice had a mild, behavioral phenotype but no axonal degeneration (Cartoni, R., Arnaud, E., Medard, J. J., Poirot, O., Courvoisier, D. S., Chrast, R., Martinou, J. C., 2010. Expression of mitofusin 2 (R94Q) in a transgenic mouse leads to Charcot-Marie-Tooth neuropathy type 2A. Brain 133, 1460-1469). Strickland et al. made a "knock-in" of the p.R94W mutation; compared to their wild type littermates, heterozygous mutant mice had no appreciable behavioral disturbance, but did have slightly thinner myelin sheaths (Strickland, A. V., Rebelo, A. P., Zhang, F., Price, J., Bolon, B., Silva, J. P., Wen, R., Züchner, S., 2014. Characterization of the mitofusin 2 R94W mutation in a knock-in mouse model. J. Periph. Nerv. Syst. 19, 152-164). Demyelinated axons, however, as well as degenerating myelinated axons, were not seen.

Surprisingly, the rat model in the present invention produced a much more robust axonopathy than did the prior mouse models. These mutant rats develop a length-dependent axonal neuropathy in the peripheral nerves and in the fasciculus gracilis. One possible explanation is that the p.R364W mutation has a more severe effect, however the mutations, p.R94W, p.R94Q, p.T105 M, and p.R364W, are also associated with a severe, early-onset axonal neuropathy in humans (Züchner, S., DeJonghe, P., Jordanova, A., Claeys, K. G., Guergueltcheva, V., Cherninkova, S., Hamilton, S. R., VanStavern, G., Krajewski, K. M., Stajich, J., Tournev, I., Verhoeven, K., Langerhorst, C. T., deVisser, M., Baas, F., Bird, T., Timmerman, V., Shy, M., Vance, J. M., 2006. Axonal neuropathy with optic atrophy is caused by mutations in mitofusin 2. Ann Neurol 59, 276-281; Züchner, S., Mersiyanova, I. V., Muglia, M., Bissar-Tadmouri, N., Rochelle, J., Dadali, E. L., Zappia, M., Nelis, E., Patitucci, A., Senderek, J., Parman, Y., Evgrafov, O., de Jonghe, P., Takahashi, Y., Tsuji, S., Pericak-Vance, M. A., Quattrone, A., Battologlu, E., Polyakov, A. V., Timmerman, V., Schroder, J. M., Vance, J. M., 2004. Mutations in the mitochondrial GTPase mitofusin 2 cause Charcot-Marie-Tooth neuropathy type 2A. Nat Genet 36, 449-451; Verhoeven, K., Claeys, K. G., Züchner, S., Schroder, J. M., Weis, J., Ceuterick, C., Jordanova, A., Nelis, E., De Vriendt, E., Van Hul, M., Seeman, P., Mazanec, R., Saifi, G. M., Szigeti, K., Mancias, P., Butler, I. J., Kochanski, A., Ryniewicz, B., De Bleecker, J., Van den Bergh, P., Verellen, C., Van Coster, R., Goemans, N., Auer-Grumbach, M., Robberecht, W., Rasic, V. M., Nevo, Y., Tournev, I., Guergueltcheva, V., Roelens, F., Vieregge, P., Vinci, P., Moreno, M. T., Christen, H. J., Shy, M. E., Lupski, J. R., Vance, J. M., De Jonghe, P., Timmerman, V., 2006. MFN2 mutation distribution and genotype/phenotype correlation in Charcot-Marie-Tooth type 2. Brain 129, 2093-2102; Chung, K. W., Kim, S. B., Park, K. D., Choi, K. G., Lee, J. H., Eun, H. W., Suh, J. S., Hwang, J. H., Kim, W. K., Seo, B. C., Kim, S. H., Son, I. H., Kim, S. M., Sunwoo, I. N., Choi, B. O., 2006. Early onset severe and late-onset mild Charcot-Marie-Tooth disease with mitofusin 2 (MFN2) mutations. Brain 129, 2103-2118; Feely, S. M. E., Laura, M., Siskind, C. E., Sottile, S., Davis, M., Gibbons, V. S., Reilly, M. M., Shy, M. E., 2011. MFN2 mutations cause severe phenotypes in most patients with CMT2A. Neurology 76, 1690-1696). It is also possible that longer axons in rats compared to mice unmask the deleterious effects of the p.R364W mutation, so that expressing the p.R94W, p.R94Q, or p.T105 M mutations in rats would produce a similar axonal neuropathy.

Pathological Findings

The model in the present invention shows actively degenerating myelinated axons and fewer myelinated axons in the distal aspect of the tibial and sural nerves, but not in distal femoral nerve which is much shorter in 40-week-old R364W mutant male rats. These findings were not present in 7-week-old rats, demonstrating that the length- and time-dependence of axonal loss in this animal model, features that are thought to be characteristic of most axonal neuropathies, including CMT2A (Lawson, V. H., Smith, A. G., Bromberg, M. B., 2003. Assessment of axonal loss in Charcot-Marie-Tooth neuropathies. Exp. Neurol. 184, 753-757; England, J. D., Gronseth, G. S., Franklin, G., Miller, R. G., Asbury, A. K., Carter, G. T., Cohen, J. A., Fisher, M. A., Howard, J. F., Kinsella, L. J., Latov, N., Lewis, R. A., Low, P. A., Sumner, A. J., 2005. Distal symmetrical polyneuropathy: Definition for clinical research. Muscle Nerve 31, 113-123; Bromberg, M. B., 2005. An approach to the evaluation of peripheral neuropathies. Semin Neurol 25, 153-159).

Further, the models in the present invention show actively degenerating myelinated axons restricted to the fasciculus gracilis in the cervical spinal cord in 40-week-old R364W mutant male rats. These findings confirm the report of axonal degeneration in the fasciculus gracilis of calves (Syring, C., Drogemuller, C., Oevermann, A., Pfister, P., Henke, D., Muller, S., Solkner, J., Leeb, T., Meylan, M., 2010. Degenerative axonopathy in a Tyrolean grey calf. J. Vet. Intern. Med. 24, 1519-1523; Drogemuller, C., Reichart, U., Seuberlich, T., Oevermann, A., Baumgartner, M., Kuhni Boghenbor, K., Stoffel, M. H., Syring, C., Meylan, M., Muller, S., Muller, M., Gredler, B., Solkner, J., Leeb, T., 2011. An unusual splice defect in the mitofusin 2 gene (MFN2) is associated with degenerative axonopathy in Tyrolean Grey cattle. PLoS One 6, e18931) and puppies (Fyfe, J. C., Al-Tamimi, R. A., Liu, J., Schaffer, A. A., Agarwala, R., Henthorn, P. S., 2011. A novel mitofusin 2 mutation causes canine fetal-onset neuroaxonal dystrophy. Neurogenetics 12, 223-232; Fyfe, J. C., AlTamimi, R. A., Castellani, R. J., Rosenstein, D., Goldowitz, D., Henthorn, P. S., 2010. Inherited Neuroaxonal Dystrophy in Dogs Causing Lethal, Fetal-Onset Motor System Dysfunction and Cerebellar Hypoplasia. J. Comp. Neurol. 518, 3771-3784) with homozygous Mfn2 mutations, although the puppies had more widespread findings. The cervical fasciculus gracilis is comprised of myelinating axons that originate from mechanoreceptors in the lumbar region (Niu, J., Ding, L., Li, J. J., Kim, H., Liu, J., Li, H., Moberly, A., Badea, T. C., Duncan, I. D., Son, Y. J., Scherer, S. S., Luo, W., 2013. Modality-based organization of ascending somatosensory axons in the direct dorsal column pathway. J. Neurosci. 33, 17691-17709), and hence are the longest sensory axons in the cervical spinal cord. The loss of axons in the dorsal columns, particularly the fasciculus cuneatus, is a consistent finding in autopsies of CMT patients (Hughes, J., Brownell, B., 1972. Pathology of peroneal muscular atrophy (Charcot-Marie-Tooth disease). J. Neurol. Neurosurg. Psychiat. 35, 648-657), including a patient with a dominant MPZ mutation causing CMT1B (Bird, T. D., Kraft, G. H., Lipe, H. P., Kenney, K. L., Sumi, S. M., 1997. Clinical and pathological phenotype of the original family with Charcot-Marie-Tooth type 1B: A 20-year study. Ann. Neurol. 41, 463-469). The axonal loss in the dorsal columns has been attributed to the loss of sensory neurons in the dorsal root ganglia (Hughes, J., Brownell, B., 1972. Pathology of peroneal muscular atrophy (Charcot-Marie-Tooth disease). J. Neurol. Neurosurg. Psychiat. 35, 648-657), but may also be attributed to, at least initially, a distal axonopathy. One expects that the loss of these centrally directed axons would contribute to diminished sensation, so that the preventing it would be a goal of therapeutic interventions.

The inventors of the present invention were surprised to find that many of the large axons in femoral motor nerves of 40-week-old R364W mutant male rats were thinly myelinated; these likely belong to alpha-motoneurons (Scherer, S. S., Xu, Y. T., Nelles, E., Fischbeck, K., Willecke, K., Bone, L. J., 1998. Connexin32-null mice develop a demyelinating peripheral neuropathy. Glia 24, 8-20). Because these axons were normally myelinated in 7-week-old mutant femoral motor nerves, the inventors suspected that these axons had been demyelinated and then remyelinated between 7 and 40 weeks. Because axonal diseases seldom cause demyelination, this finding suggests that the R364W mutation has direct effects on myelinating Schwann cells.

There is little precedent for demyelination in CMT2A patients themselves. Chung et al. biopsied 2 individuals from 2 different families with the p.R364W mutation (Chung, K. W., Kim, S. B., Park, K. D., Choi, K. G., Lee, J. H., Eun, H. W., Suh, J. S., Hwang, J. H., Kim, W. K., Seo, B. C., Kim, S. H., Son, I. H., Kim, S. M., Sunwoo, I. N., Choi, B. O., 2006. Early onset severe and late-onset mild Charcot-Marie-Tooth disease with mitofusin 2 (MFN2) mutations. Brain 129, 2103-2118) Like other mutations associated with severe, early-onset axonal neuropathy, the chief finding was severe axonal loss; one biopsy also showed clusters of regenerated axons. Similarly, the electrophysiological analysis of individuals with a R364W mutation is consistent with axonal loss, and little evidence of demyelination (Chung, K. W., Kim, S. B., Park, K. D., Choi, K. G., Lee, J. H., Eun, H. W., Suh, J. S., Hwang, J. H., Kim, W. K., Seo, B. C., Kim, S. H., Son, I. H., Kim, S. M., Sunwoo, I. N., Choi, B. O., 2006. Early onset severe and late-onset mild Charcot-Marie-Tooth disease with mitofusin 2 (MFN2) mutations. Brain 129, 2103-2118; Feely, S. M. E., Laura, M., Siskind, C. E., Sottile, S., Davis, M., Gibbons, V. S., Reilly, M. M., Shy, M. E., 2011. MFN2 mutations cause severe phenotypes in most patients with CMT2A. Neurology 76, 1690-1696). There are reports of "some myelin sheaths being disproportionately thin" (Verhoeven, K., Claeys, K. G., Züchner, S., Schroder, J. M., Weis, J., Ceuterick, C., Jordanova, A., Nelis, E., De Vriendt, E., Van Hul, M., Seeman, P., Mazanec, R., Saifi, G. M., Szigeti, K., Mancias, P., Butler, I. J., Kochanski, A., Ryniewicz, B., De Bleecker, J., Van den Bergh, P., Verellen, C., Van Coster, R., Goemans, N., Auer-Grumbach, M., Robberecht, W., Rasic, V. M., Nevo, Y., Tournev, I., Guergueltcheva, V., Roelens, F., Vieregge, P., Vinci, P., Moreno, M. T., Christen, H. J., Shy, M. E., Lupski, J. R., Vance, J. M., De Jonghe, P., Timmerman, V., 2006. MFN2 mutation distribution and genotype/phenotype correlation in Charcot-Marie-Tooth type 2. Brain 129, 2093-2102), and of "onion-bulbs" in biopsies from CMT2A patients (Vallat, J. M., Ouvrier, R. A., Pollard, J. D., Magdelaine, C., Zhu, D., Nicholason, G. A., Grew, S., Ryan, M. M., Funalot, B., 2008. Histopathological findings in hereditary motor and sensory neuropathy of the axonal type with onset in early childhood associated with Mitofusin 2 mutations. J Neuropathol Exp Neurol 67, 1097-1102), but these are inconspicuous and could represent the after effects of axonal degeneration and regeneration. Similarly, there are reports of intermediately slowed conductions in CMT2A patients (30-40 m/sec in motor nerves in the arms), but these findings do not make a strong case for a primary demyelinating neuropathy. Whether demyelination is an early feature of some CMT2A patients remains to be determined.

Behavioral Assessment R364W Mutants

Given the severity of neuropathy at 40 weeks, the inventors with partial confirmation anticipated that the longitudinal analysis of behavioral profiling would reveal a progressive deterioration of sensory and motor function in R364W mutant rats. The hotplate test did not detect a deficit, raising the possibility that C-fiber function is relatively preserved. Further advanced testing will be required to evaluate effects of the R364W mutation on myelinated and unmyelinated sensory axons, as the hotplate test does not discriminate between threshold and amplitude changes in thermal sensitivity. It was also perplexing that the weakness in both forelimb and hindlimb grip strength was observed at the earliest age tested (7 weeks), but not at older ages (25 and 52 weeks), when the neuropathy becomes more pronounced in pathological analysis. Similarly, gross measurement of motor function in rotarod and tapered balance beam testing did not reveal age- or genotype-specific changes in motoric function. These findings motivated performance to be assessed in the horizontal ladder test, which is able to measure subtle motor coordination effects by looking at footslips, and this test showed significant deficits in hind limb performance at 30 weeks of age, which greatly worsened at advanced age (one year). The sensitive multi-parametric gait analysis using the automated NeuroCube® (PsychoGenics, Inc. Tarrytown New York) imaging-based system demonstrated severely affected gait performance that was further revealed to represent paw positioning and presentation (as measured via paw imaging), and an unstable, hesitant and splayed pattern of leg movement.

H361Y mutant rats also demonstrated abnormal gait and body movement at 8 and 16 weeks. H361Y mutant rats showed abnormalities in gait dynamics. A shorter stand duration in both forelimbs and hind limbs were detected at 8 weeks. In addition, H361Y mutant animals showed increased base width, of the forelimbs at 8 weeks although changes in hind limb base width were not detected at this time point. At 16 weeks, H361Y mutant rats showed changes in gait dynamics. A shorter stand duration in both forelimbs and hind limbs was detected, similar to observations at 8 weeks. In addition, mutant animals showed increased step lengths and swing duration which indicate a lengthening of the gait cycle.

These changes may indicate a faster gait cycle with the appearance of earlier deficits in the forelimbs.

The behavioral changes in mutant rats were progressive, with strong significance achieved with multiple gait measures at one year of age, and early progressive change (7-19 weeks of age in the R364W mutants) observed for fine measures of paw positioning and imaging.

The contents of the articles, patents, and patents applications and all other documents and electronically available information mentioned or cited herein, are hereby incorporated by reference in their entirety to the same extent as if each individual publication was specifically and individually indicated to be incorporated by reference.

The terms and expressions used herein have been used as terms of description and not of limitation, and there is no intention in the use of such terms of excluding any equivalents of the features shown and described or portions thereof. It is recognized that various modification are possible within the scope of the invention claimed. Thus, it should be understood that although the present invention has been specifically disclosed by preferred embodiments and other features, modification and variation of the invention embodied therein herein disclosed may be used by those skilled in the art, and that such modification and variations are considered to be within the scope of this invention.

What is claimed is:

1. A method for determining whether a compound is potentially useful for treating humans having Charcot-Marie-Tooth disease 2A, comprising:

a. providing a genetically modified non-human knock-in rat whose genome comprises genetically modified mitofusin2 gene encoding mutant protein comprising Arg364Trp or His361Tyr mutation, or progenies thereof, and the genetically modified non-human knock-in rat exhibits peripheral motor nerve cell axons and Schwann cells having a spatially, and age-dependent progressive degeneration;

b. contacting the genetically modified non-human knock-in rat with the compound; and c. monitoring phenotypic expression of the non-human knock-in rat, such that a change in activity in response to the compound indicates that the compound is potentially useful for treating or alleviating the symptoms of Charcot-Marie-Tooth disease 2A.

2. The method of claim 1 wherein the non-human knock-in rat is monitored for functional abnormalities in gait dynamics, representing gait deficits as experienced in CMT2A patients.

3. The method of claim 1 wherein the non-human knock-in rat is monitored for functional abnormalities in hind limb balance performance in a horizontal ladder test, representing balance deficits as experienced by CMT2A patients.

4. The method of claim 1 wherein the non-human knock-in rat is B monitored for changes in density of myelinated axons and actively degenerating myelinated axons at different ages, representing age-dependent progressive degeneration as experienced by CMT2A patients.

5. The method of claim 1 wherein the non-human knock-in rat is monitored for changes in density of myelinated axons and actively degenerating myelinated axons at different distances distal to the spinal cord, and compared with unaffected sensory nerve tracts of peripheral nerve, representing length-dependent progressive degeneration as experienced by CMT2A patients.

* * * * *

SEQUENCE LISTING

```
<160> NUMBER OF SEQ ID NOS: 7

<210> SEQ ID NO 1
<211> LENGTH: 122
<212> TYPE: DNA
<213> ORGANISM: Rattus rattus

<400> SEQUENCE: 1
gagtgcattt cccagtctgc agtaaagacc aaatttgagc agcacacagt ccgggccaag      60
cagattgcag aggccgtccg tctcatcatg gattccctgc acattgcggc tcaggagcag     120
cg                                                                    122

<210> SEQ ID NO 2
<211> LENGTH: 122
<212> TYPE: DNA
<213> ORGANISM: Rattus rattus

<400> SEQUENCE: 2
gagtgcattt cccagtctgc agtaaagacc aaatttgagc agcacacagt ctgggctaag      60
cagattgcag aggccgtccg tctcatcatg gattccctgc acattgcggc tcaggagcag     120
cg                                                                    122

<210> SEQ ID NO 3
<211> LENGTH: 20
<212> TYPE: DNA
<213> ORGANISM: Rattus rattus

<400> SEQUENCE: 3
cgagaggcga tttgaggtaa                                                  20

<210> SEQ ID NO 4
```

```
<211> LENGTH: 20
<212> TYPE: DNA
<213> ORGANISM: Rattus rattus

<400> SEQUENCE: 4
ctgaccagtg tgaccaggtg                                                   20

<210> SEQ ID NO 5
<211> LENGTH: 122
<212> TYPE: DNA
<213> ORGANISM: Rattus rattus

<400> SEQUENCE: 5
gagtgcattt cccagtctgc agtaaagacc aaatttgagc agtatacagt gcgggccaag        60
cagattgcag aggccgtccg tctcatcatg gattccctgc acattgcggc tcaggagcag       120
cg                                                                     122

<210> SEQ ID NO 6
<211> LENGTH: 20
<212> TYPE: DNA
<213> ORGANISM: Rattus rattus

<400> SEQUENCE: 6
cgagaggcga tttgaggtaa                                                   20

<210> SEQ ID NO 7
<211> LENGTH: 19
<212> TYPE: DNA
<213> ORGANISM: Rattus rattus

<400> SEQUENCE: 7
ctgaccagtg gaccaggtg                                                    19
```